United States Patent
Leisinger et al.

(10) Patent No.: US 7,927,376 B2
(45) Date of Patent: Apr. 19, 2011

(54) EXPANDABLE ACETABULAR LINER EXTRACTION DEVICE, CUP ASSEMBLY AND ASSOCIATED METHOD

(75) Inventors: Steven R. Leisinger, Silver Lake, IN (US); James A. Caywood, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 492 days.

(21) Appl. No.: 11/171,908

(22) Filed: Jun. 30, 2005

(65) Prior Publication Data

US 2007/0005144 A1    Jan. 4, 2007

(51) Int. Cl.
*A61F 2/30* (2006.01)
(52) U.S. Cl. .................. 623/23.43; 606/99; 606/91
(58) Field of Classification Search .......... 606/81, 606/91, 99, 86 A, 86 B; 623/22.21–22.39; 29/265; 81/445

See application file for complete search history.

(56) References Cited

U.S. PATENT DOCUMENTS

| | | |
|---|---|---|
| 2,031,998 A | 7/1934 | Bliss |
| 3,412,733 A | 11/1968 | Ross |
| 3,702,611 A | 11/1972 | Fishbein |
| 4,694,569 A | 9/1987 | Colvell et al. |
| 4,795,469 A | 1/1989 | Oh |
| 4,955,919 A * | 9/1990 | Pappas et al. .............. 623/22.26 |
| 5,098,437 A * | 3/1992 | Kashuba et al. ............ 606/89 |
| 5,112,338 A | 5/1992 | Anspach, III |
| 5,282,864 A | 2/1994 | Noiles et al. |
| 5,649,931 A | 7/1997 | Bryant et al. |
| 5,938,701 A | 8/1999 | Hiernard et al. |
| 6,063,123 A | 5/2000 | Burrows et al. |
| 6,132,469 A | 10/2000 | Schroeder |
| 6,228,900 B1 | 5/2001 | Shen et al. |
| 6,286,401 B1 | 9/2001 | Hajianpour |
| 6,383,188 B2 * | 5/2002 | Kuslich et al. ............. 606/80 |
| 6,451,058 B2 * | 9/2002 | Tuke et al. ............. 623/22.21 |
| 6,488,713 B1 | 12/2002 | Hershberger |
| 6,565,573 B1 | 5/2003 | Ferrante et al. |
| 6,602,260 B2 | 8/2003 | Harari et al. |
| 7,003,877 B2 | 2/2006 | Reale |
| 2006/0276797 A1 * | 12/2006 | Botimer ................ 606/81 |
| 2007/0010816 A1 | 1/2007 | Wilkinson et al. |
| 2007/0010825 A1 * | 1/2007 | Leisinger et al. ........... 606/99 |

FOREIGN PATENT DOCUMENTS

| | | |
|---|---|---|
| DE | 4429026 A1 | 2/1995 |
| DE | 29516473 U1 | 10/1995 |
| EP | 1 000 595 A1 | 5/2000 |

OTHER PUBLICATIONS

Non-Final Rejection—Jan. 5, 2007—U.S. Appl. No. 11/171,616.
Final Rejection—Aug. 20, 2007—U.S. Appl. No. 11/171,616.
Non-Final Rejection—Mar. 24, 2008—U.S. Appl. No. 11/171,616.
Non-Final Rejection—Sep. 19, 2008—U.S. Appl. No. 11/171,616.
Final Rejection—Feb. 27, 2009—U.S. Appl. No. 11/171,616.
Non-Final Rejection—Aug. 19, 2009—U.S. Appl. No. 11/171,616.

* cited by examiner

*Primary Examiner* — Thomas C Barrett
*Assistant Examiner* — Michael J Araj

(57) ABSTRACT

An extraction device for removing a liner from an acetabular cup is provided. The extraction device includes a body and an actuator. The actuator is operably connected to the body. The extraction device also includes a jaw for cooperation with the liner. The jaw includes a portion of the jaw for penetrating into the liner. The jaw is operably connected to the actuator. The actuator is adapted to cooperate with the jaw to provide a first position for the jaw spaced from the liner and a second position for the jaw in contact with the liner.

15 Claims, 29 Drawing Sheets

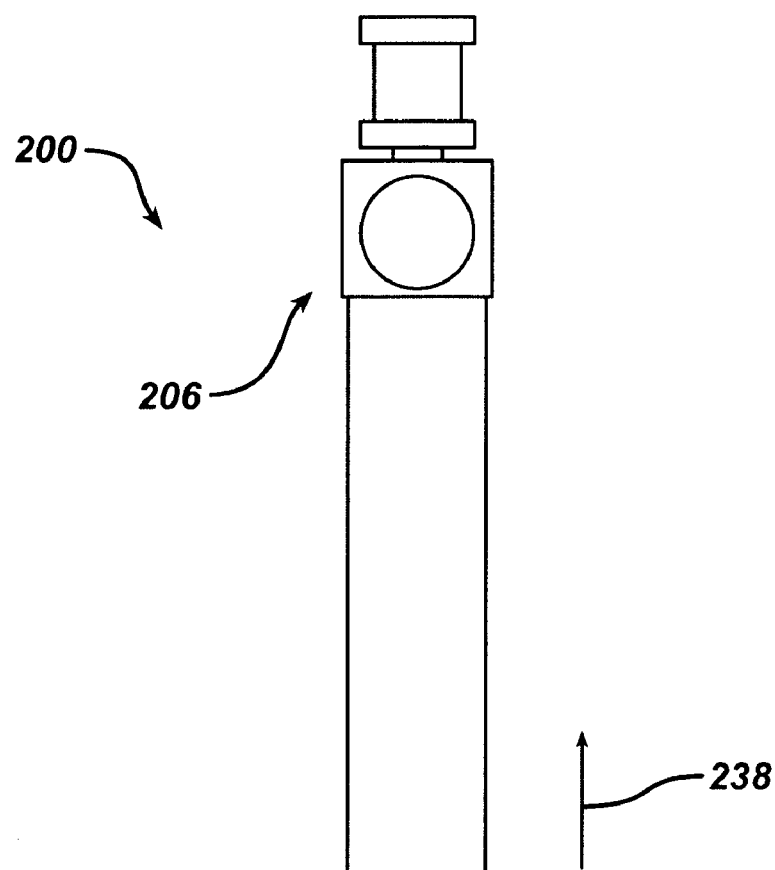
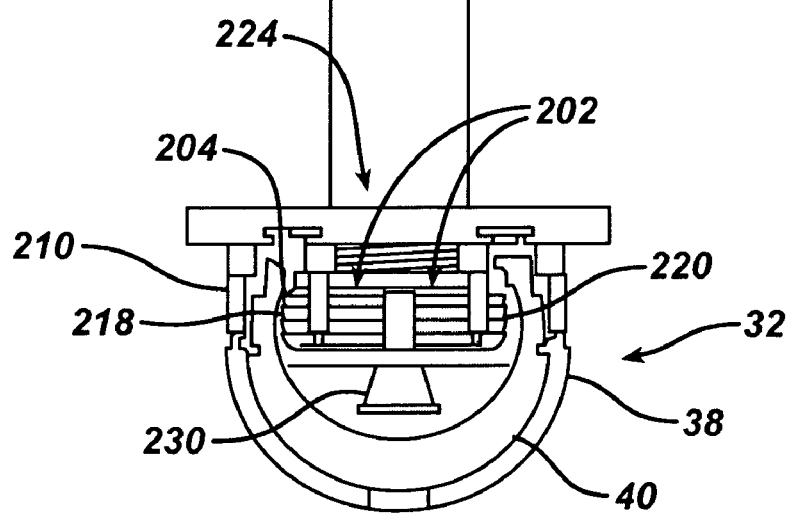
FIG. 15

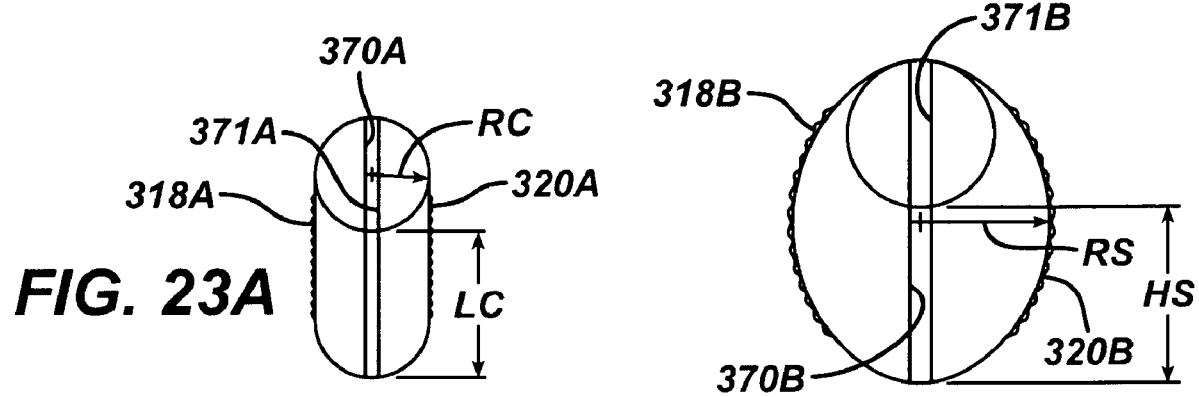
FIG. 23A
FIG. 23B
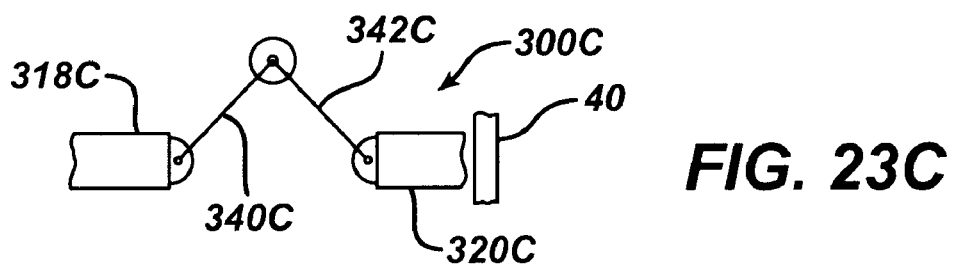
FIG. 23C
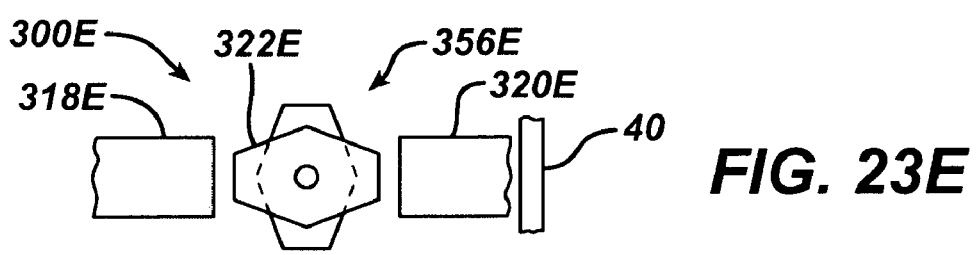
FIG. 23E
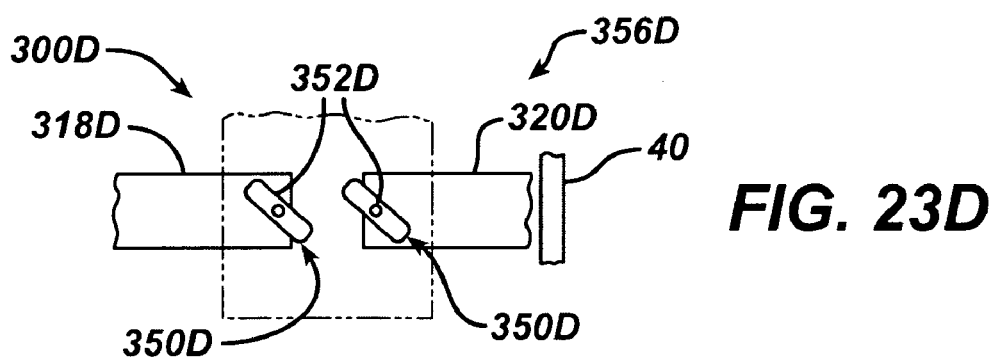
FIG. 23D
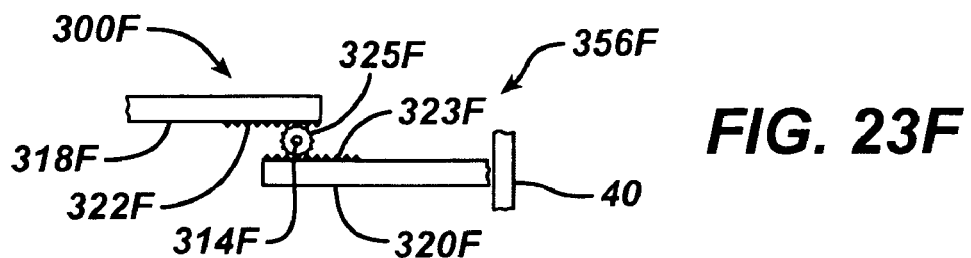
FIG. 23F

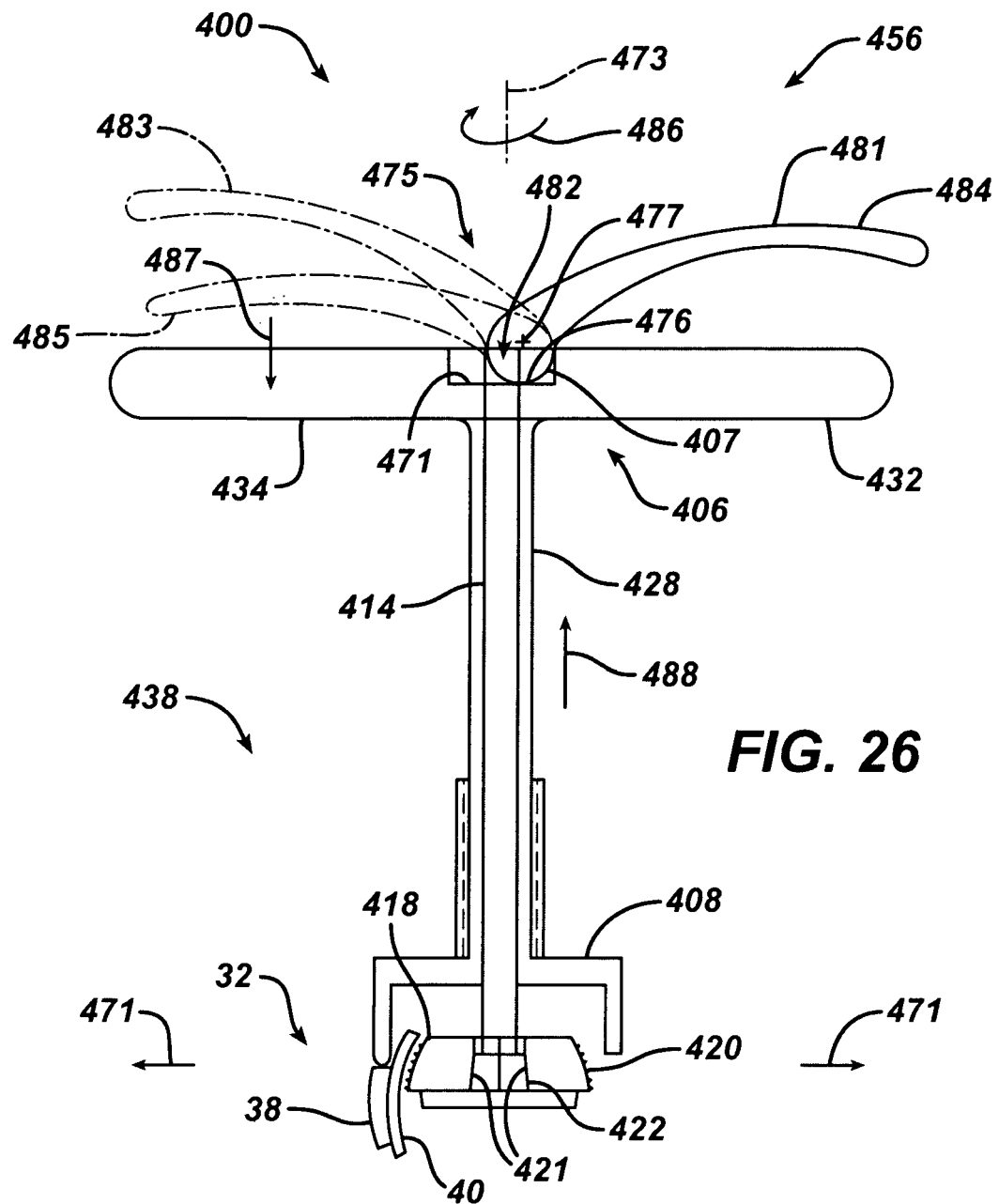
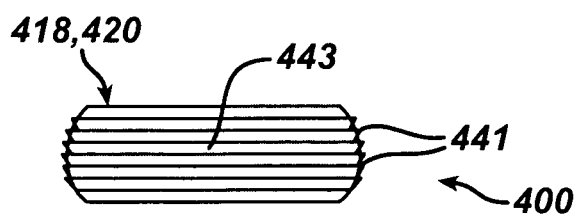
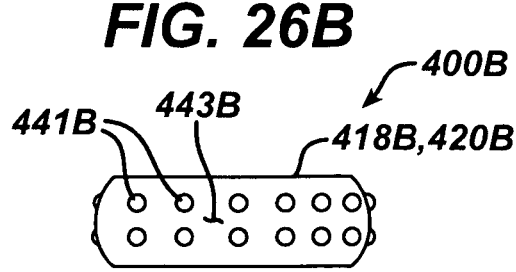

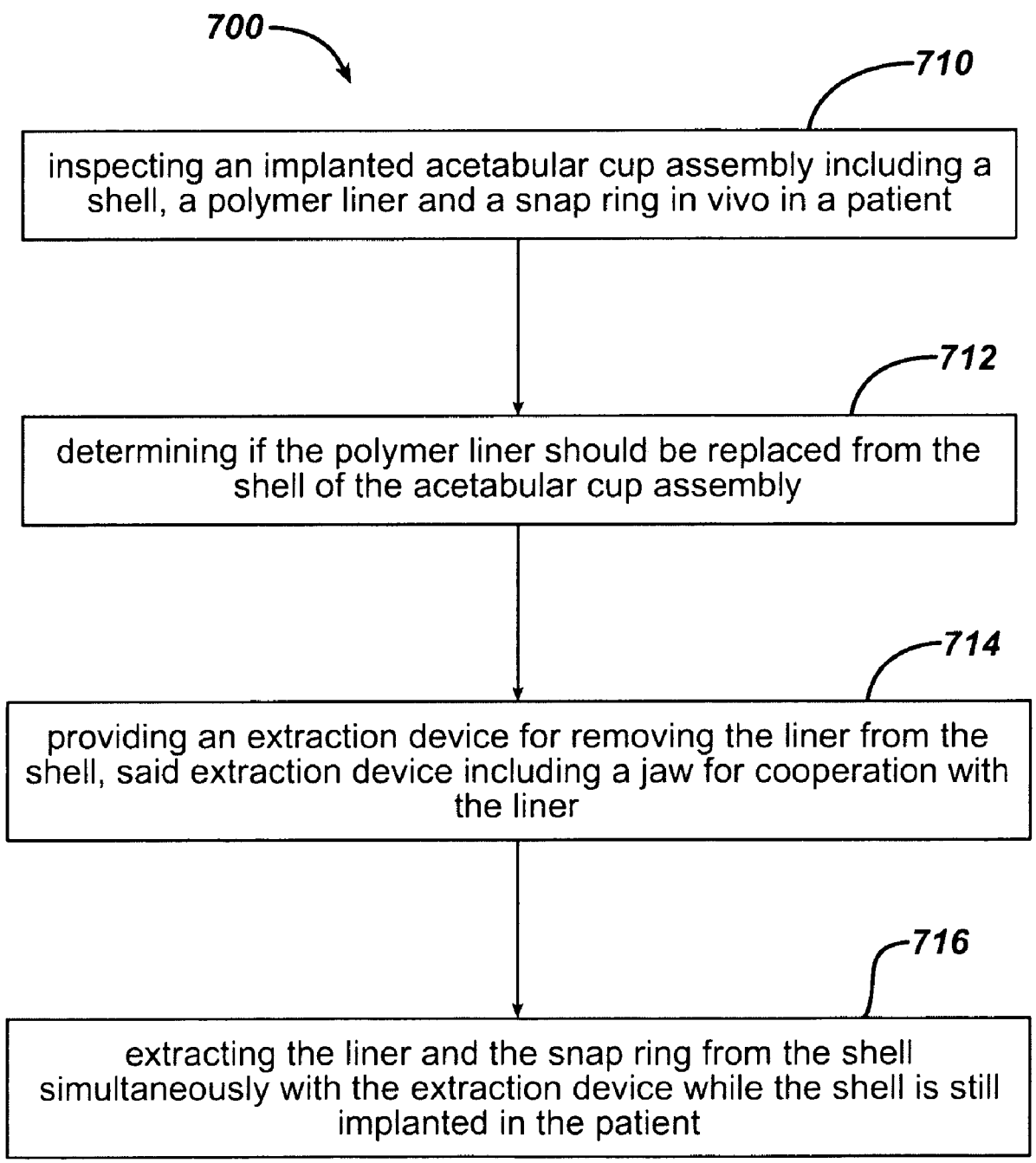

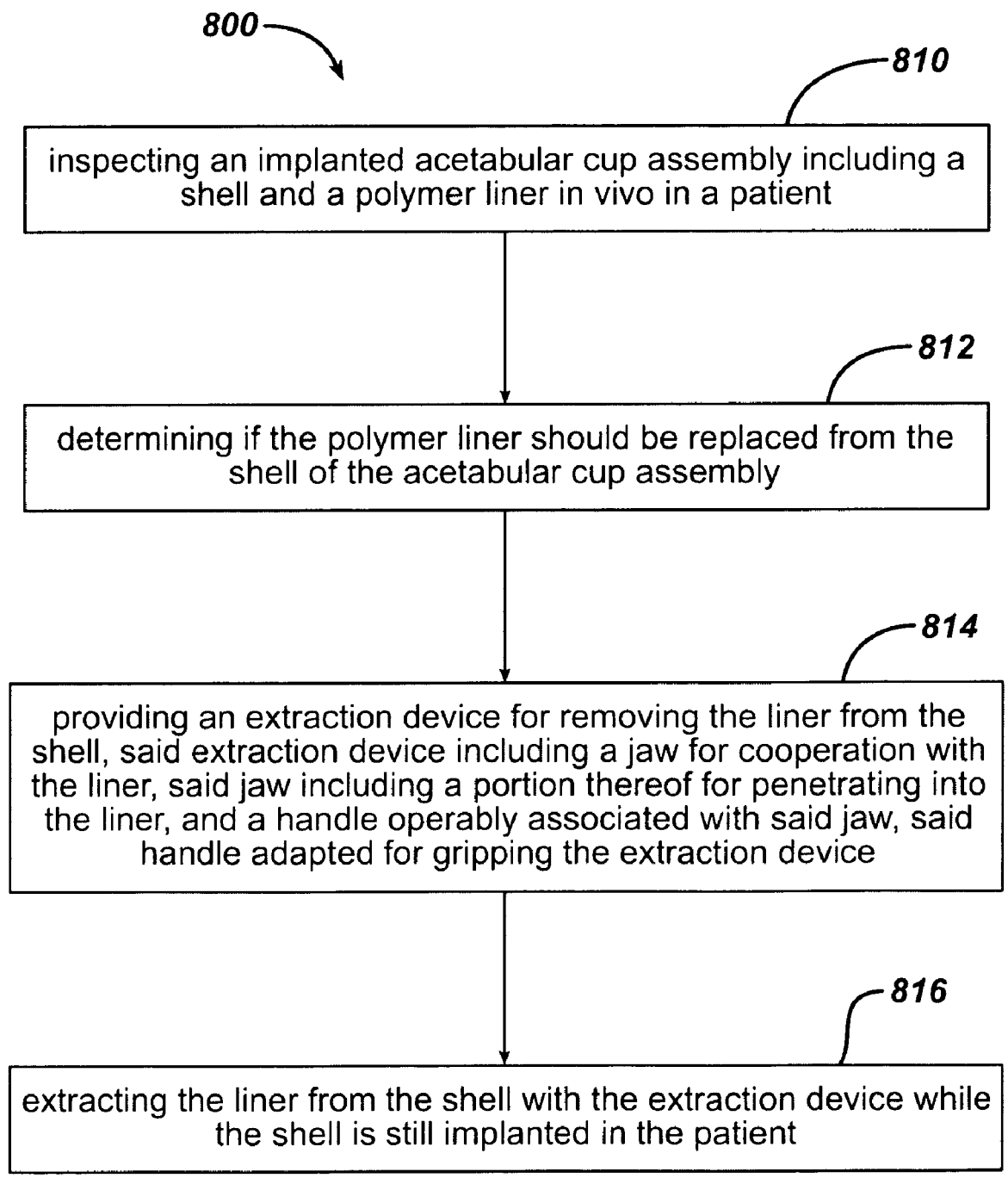

EXPANDABLE ACETABULAR LINER EXTRACTION DEVICE, CUP ASSEMBLY AND ASSOCIATED METHOD

CROSS-REFERENCE TO RELATED APPLICATIONS

Cross reference is made to the following application: U.S. Pat. No. 7,785,331, titled "ACETABULAR LINER EXTRACTION DEVICE, KIT AND ASSOCIATED METHOD" filed concurrently herewith which is incorporated herein by reference.

TECHNICAL FIELD OF THE INVENTION

The present invention relates generally to the field of orthopaedics, and more particularly, to an instrument for use in arthroplasty.

BACKGROUND OF THE INVENTION

A joint within the human body forms a juncture between two or more bones or other skeletal parts. The ankle, hip, knee, shoulder, elbow and wrist are just a few examples of the multitude of joints found within the body. As should be apparent from the above list of examples of joints, many of the joints permit relative motion between the bones. For example, the motion of sliding, gliding, and hinge or ball and socket movements may be incorporated into a joint. For example, the ankle permits a hinge movement, the knee allows for a combination of gliding and hinge movements and the shoulder and hip permit movement through a ball and socket arrangement.

The joints in the body are stressed or can be damaged in a variety of ways. For example, the gradual wear and tear is imposed on the joints through the continuous use of a joint over the years. The joints that permit motion have cartilage positioned between the bones providing lubrication to the motion and also absorbing some of the forces direct to the joint. Over time, the normal use of a joint may wear down the cartilage and bring the moving bones in a direct contact with each other. In contrast, in normal use, a trauma to a joint, such as the delivery of a large force, from an accident for, example, an automobile accident, may cause considerable damage to the bones, the cartilage or to other connective tissue such as tendons or ligaments.

Arthropathy, a term referring to a disease of the joint, is another way in which a joint may become damaged. Perhaps the known joint disease is arthritis, which is generally referred to a disease or inflammation of a joint that results in pain, swelling, stiffness, instability, and often deformity.

There are many different forms of arthritis, with osteoarthritis being the most common and resulting from the wear and tear of a cartilage within a joint. Another type of arthritis is osteonecrosis, which is caused by the death of a part of the bone due to loss of blood supply. Other types of arthritis are caused by trauma to the joint while others, such as rheumatoid arthritis, Lupus, and psoriatic arthritis destroy cartilage and are associated with the inflammation of the joint lining.

The hip joint is one of the joints that is commonly afflicted with arthropathy. The hip joint is a ball and socket joint that joins the femur or thighbone with the pelvis. The pelvis has a semispherical socket called the acetabulum for receiving a ball socket head in the femur. Both the head of the femur and the acetabulum are coated with cartilage for allowing the femur to move easily within the pelvis. Other joints commonly afflicted with arthropathy include the spine, knee, shoulder, carpals, metacarpals, and phalanges of the hand. Arthroplasty as opposed to arthropathy commonly refers to the making of an artificial joint. In severe cases of arthritis or other forms of arthropathy, such as when pain is overwhelming or when a joint has a limited range of mobility, a partial or total replacement of the joint within an artificial joint may be justified. The procedure for replacing the joint varies, of course, with the particular joint in question, but in general involves replacing a terminal portion of an afflicted bone with a prosthetic implant and inserting a member to serve as a substitute for the cartilage.

The prosthetic implant is formed of a rigid material that becomes bonded with the bone and provides strength and rigidity to the joint and the cartilage substitute members chosen to provide lubrication to the joint and to absorb some of the compressive forces. Suitable material for the implant include metals, ceramics, composites and metals, for example, a titanium alloy, a cobalt chromium alloy, and a stainless steel alloy. Suitable materials for cartilage substitutes include polyethylene. A cement may also be used to secure the prosthetic implant to the host bone.

A total hip replacement, for example, involves removing the ball shaped head of the femur and inserting a stem implant into the center of the bone, which is referred to as the medullary canal, or marrow of the bone. The stem implant may be cemented into the medullary canal or may have a porous coated surface for allowing the bone to heal directly to the implant.

The stem implant has a neck and a ball shaped head, which are intended to perform the same functions as a healthy femur's neck and a ball shaped head. The polyethylene cup is inserted into the acetabulum and has a socket for receiving the head on the stem implant.

The invention relates to a surgical instrument for releasing the press fit of a joint insert in a joint socket.

Joint inserts are often held by a cone-type press fit in joint sockets, for example, in hip joint sockets. In order to release such joint inserts from the joint socket again, it is either necessary to destroy the joint inserts or to provide special devices on the joint socket which enable ejection of the joint insert from the joint socket. For example, DE 295 16 473 U1 describes a screw arrangement on the joint socket with which the joint insert can be pressed out of the joint socket. However, this makes it necessary for the joint socket to be of appropriate design and for an opening to be left in the joint insert.

An acetabular hip prosthesis has various design alternatives within their design and construction. One such design alternative has to do with whether the hip prosthesis is constrained or unconstrained. Similarly, a hip prosthesis, including a ball attached to a stem, is inserted into the canal of the resected femur and a socket including a portion of a spherical pocket is secured to the acetabulum. The portion of the ball in contact with the acetabular liner may represent less than 50% or a hemisphere of the head. In such an arrangement the head may freely be positioned in the liner. Alternatively, the acetabular component may extend around the head of the femur for an amount greater than 180°. In such a configuration the head may not freely be removed from the acetabular component. Such a construction is defined as a constrained prosthesis.

Referring now to FIG. 3, a prior art unconstrained prosthesis is shown as prosthesis 10. The prosthesis 10 includes a stem 12 and a head 14. The stem 14 is placed within femur 2. The head 14 matingly fits with liner 16, which is fitted within cup 18. The cup 18 is secured to acetabulum 4 of the patient. The liner 16 and the head 14 define a contact area therebetween having an included angle β, which is less 180°. Since β is less than 180°, the head 14 may freely move in and out of the liner 16.

It should be appreciated that use of an unconstrained liner may make a dislocation of the hip possible for the patient. If excessive extension of the leg is made by the patient, the head 14 may slip from the liner 14 and a dislocation or a misplacement of the head 14 may occur. If a dislocation has occurred, discomfort may accompany such dislocation and a surgical procedure to relocate the hip may be necessary.

The unconstrained hip prosthesis 10 as shown in FIG. 3, does however have the advantage of increased range of motion. The range of motion of the hip prosthesis 10 may be defined by an angle α and θ that represents the motion between the hip stem 12 and the liner 16 that can occur.

To avoid problems of dislocation of the head of the femur, prostheses have been provide for increased anglar contact between the liner and the head of the prosthesis. Such prosthesis are called constrained prosthesis. Constrained prosthesis prevent the occurrence of dislocation of the head of the prosthesis.

Referring now to FIG. 4, a constrained prosthesis 10' is shown. The prosthesis 10' includes a stem 12' similar to the stem in FIG. 3. The stem 12' has a head 14' secured thereto. The head 14 may be similar to the head 14' OF FIG. 3. The prosthesis 10' further includes a cap 18 to which a liner 16' is secured. The cap 18' is secured to acetabulum 4 of the patient. The stem 12' is secured to femur 2 of the patient similarly.

The liner 16 is somewhat different than the liner 16 of the prosthesis 10 of FIG. 3. The liner 16' is a constrained liner. In other words, the liner 16' contacts the head 14' of the prosthesis 10' at a contact angle θ' which is greater than 180°. Since the contact angle between the head 14' and liner 16' is greater than 180°, the dislocation of the hip prosthesis 10' is much less likely.

The head 14' may be placed in the liner 16' utilizing different techniques. For example, the liner 16' may include a series of slits in the distal end thereof, which permit the distal portion of the liner 16' to open until the head 14' is assembled. After the head 14' is assembled into the liner 16,' a constraining ring 20' may be positioned on the liner 16'.

To prevent the liner 16' from being separated from the cap 18', the liner 16' may include an additional feature to secure the liner 16' to the cap 18'. For example, the cap and liner may include grooves 22' and 24' respectively, for receiving a snap ring 26' to be secured there between.

During revision surgery it may be necessary for a liner Δ to be removed from the prosthesis and be replaced with a new liner. The cap and stem may remain in the patient. The liner, thus, may need to be removed from the cap.

To remove a liner from the cap of an unconstrained prosthesis 10 as shown in FIG. 3, various devices are available for removing the liner. For example, a suction cup may be utilized to remove the liner from the cap or the liner may simply fall out in that it is not permanently secured to the cap 18. Alternatively, a screw 28 may be utilized to separate the liner from the cap as shown in U.S. Pat. No. 5,282,864 to Noiles, et al.

The removal of a liner from the constrained prosthesis 10' of FIG. 4 is more difficult. The snap ring makes the removal of the constrained liner 16' quite troublesome.

Attempts have been made to remove the locking ring from the grooves of the liner and shell by contracting the locking ring and then lifting the liner from the shell. Attempts of contracting the locking ring have proved unsuccessful because the locking ring may be inaccessible and difficult to compress in situ with the prosthesis in the patient.

Another attempt at removing the locking ring, including driving screws through the liner in hopes that the locking mechanism would break and lift the liner from the shell. The reaction force of the screw and the shells may be sufficient to overcome the force of the locking mechanism.

Another attempt to remove the liner from the shell was to cut the liner from the shell. Tools that are designed to cut liners may not be deep enough to expose the locking ring. Also, the use of a tool to cut the liner may raise concerns of creating polyethylene debris in the incision, which may prove to be problematic in that such debris may contribute to osteolysis.

This invention relates to the surgical instrument for removing the liner from the shell in situ in a patient where the forces necessary to separate the liner from the shell may be quite large.

SUMMARY OF THE INVENTION

Instrument of the present invention is utilized to contract the locking ring and cause it to buckle or rotate such that the liner may be lifted out of the shell. The instrument of the present invention accomplishes the contracting and buckling of the locking ring by laterally expanding with a gripping device in the liner and lifting the liner out of the shell with sufficient force to cause the locking ring to buckle and collapse.

The device in the form of an instrument of the present is inserted into a liner and a gripping mechanism in the form of, for example, teeth that are expanded laterally into the polyethylene liner to hold the removal tool in place. Once the griping mechanism is in place, expanded into the polyethylene liner and axial tension force is applied, the force applied via a mechanism, for example, a screw or a cam-lever mechanism, causing the locking ring to buckle and collapse. The ring collapses into a position such that the locking ring may pass by the groove of the shell and permit the lifting of the liner from the shell.

According to one embodiment of the present invention, there is provided an extraction device for removing a liner from an acetabular cup. The extraction device includes a jaw and a handle. The jaw is for cooperation with the liner and including a portion of the jaw for penetrating into the liner. The handle is operably associated with the jaw and is adapted for gripping the extraction device.

According to another embodiment of the present invention there is provided an extraction device for removing a liner and a snap ring simultaneously from an acetabular cup. The liner is fitted into an inner periphery of the cup and the snap ring is fitted into a groove in the inner periphery of the cup. The extraction device includes a jaw and a handle. The jaw is for cooperation with the liner and includes a portion of the jaw for penetrating into the liner. The handle is operably associated with the jaw and is adapted for gripping the extraction device. The handle and the jaw are adapted to provide sufficient penetration of the jaw into the liner to permit the snap ring to be buckled out of the groove and removed simultaneously with the liner.

According to yet another embodiment of the present invention there is provided an extraction device for removing a liner from an acetabular cup. The extraction device includes a body and an actuator. The actuator is operably connected to the body. The extraction device also includes a jaw for cooperation with the liner. The jaw includes a portion of the jaw for penetrating into the liner. The jaw is operably connected to the actuator. The actuator is adapted to cooperate with the jaw to provide a first position for the jaw spaced from the liner and a second position for the jaw in contact with the liner.

According to another embodiment of the present invention there is provided a kit for use in revision hip surgery. The kit includes an extraction device for removing a liner from an acetabular cup. The extraction device includes a jaw for cooperation with the liner. The jaw includes a portion of the jaw for penetrating into the liner. The extraction device also includes a handle operably associated with the jaw. The handle is adapted for gripping the extraction device. The kit also includes a polymer revision cup and a snap ring.

According to yet another embodiment of the present invention there is provided a cup assembly including a metal shell having an internal groove and a polymer liner fitted into the shell. The cup assembly also includes a snap ring fitted into the shell. At least the shell, the liner or the snap ring or more than one are adapted to permit the snap ring to be removed from the shell simultaneously with the polymer liner.

According to a further embodiment of the present invention, there is provided a method for performing orthopaedic revision surgery. The method includes the steps of inspecting an implanted acetabular cup assembly including a shell and a polymer liner in vivo in a patient and determining if the polymer liner should be replaced from the shell of the acetabular cup assembly. The method also includes the step of providing an extraction device for removing the liner from the shell. The extraction device includes a jaw for cooperation with the liner. The jaw includes a portion of the jaw for penetrating into the liner. The extraction device also includes a handle operably associated with the jaw. The handle is adapted for gripping the extraction device. The method also includes the step of extracting the liner from the shell with the extraction device while the shell is still implanted in the patient.

According to a further embodiment of the present invention, there is provided a method for performing orthopaedic revision surgery. The method includes the steps of inspecting an implanted acetabular cup assembly including a shell, a polymer liner and a snap ring in vivo in a patient and determining if the polymer liner should be replaced from the shell of the acetabular cup assembly. The method also includes the step of providing an extraction device for removing the liner from the shell. The extraction device includes a jaw for cooperation with the liner. The method also includes the step of extracting the liner and the snap ring from the shell simultaneously with the extraction device while the shell is still implanted in the patient.

The technical advantages of the present invention include the ability to remove the liner without disabling of the locking mechanism. For example, according to one aspect of the present invention an extraction device for removing a liner for an acetabular cup is provided where in the acetabular cup includes a retaining ring to retain the liner to the cup. The extraction device includes a jaw that cooperates with a liner. The jaw includes a portion for penetrating into the liner. The extraction device further includes a handle connected to a jaw for gripping with the distraction device. Thus, the present invention provides for an ability to remove the liner without the disabling the locking mechanism.

The technical advantages of the present invention further include the ability to remove the liner without creating polyethylene debris. For example and according to another aspect of the present invention, an extraction device is provided for removing a liner from an acetabular cup. The liner includes a locking ring, a jaw for cooperation with the liner, and a handle associated with the jaw. The jaw penetrates the liner and then the handle is used to grip the distraction device and pull the liner from the cup. The jaw engages the liner with sufficient depth such that the jaw has enough force transferring capacity to permit the locking ring to twist and contract such that the locking ring and liner may be pulled from the acetabular cup. Thus, the present invention provides for an ability to remove the liner without creating polyethylene debris.

The technical advantages of the present invention further include the ability to remove the liner from a cup having a locking ring in one step. For example, according to yet another aspect of the present invention, an extraction device is provided for removing a liner from a cup having a retaining ring. The device includes a jaw for penetrating the liner and a handle connected to the jaw. The handle is used to pull the liner from the cup. Thus, the present invention provides for the ability to remove the liner from the cup in one step.

The technical advantages of the present invention, further include quick and easy removal of a liner from an acetabular cup when the cup and liner are connected with a retaining ring. For example, according to another aspect of the present invention, a method for performing a hip arthroplasty includes a step in which the extraction device is provided with a jaw and a handle. The jaw is penetrated into the liner. The handle, which is connected to the jaw, is used to pull the liner from the cup. The force of liner being pulled from the cup causes the retaining ring to buckle progress inwardly such that the liner and retaining ring may be extracted from the cup. Thus, the present invention provides for a quick and easy method for removing a liner from a cup having a retaining ring.

The technical advantages of the present invention further include the ability to provide an extraction device for removing a liner from an acetabular cup that is easy to manufacture. For example, according to one aspect of the present invention, an extraction device for removing a liner from a cup includes a jaw having a portion for penetrating the liner and a handle associated with the jaw. Thus, the present invention provides for an extraction device that is easy to manufacture and has few moving parts.

The technical advantages of the present invention further include the ability to easily clean and sterilize the extraction device. For example, according to yet another aspect of the present invention, an extraction device is provided with a jaw for cooperation with a separable body and a handle removably connected to the body. Thus, the present invention provides for an extraction device with an ability to easily clean and sterilize the extraction device.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 15 is a plan view, partially in cross section, of the acetabular liner extraction device of FIG. 9;

FIG. 23A is a partial plan view of another embodiment of the device of the present invention;

FIG. 23B is a partial plan view of another embodiment of the device of the present invention;

FIG. 23C is a partial plan view of another embodiment of the device of the present invention;

FIG. 23D is a partial plan view of another embodiment of the device of the present invention;

FIG. 23E is a partial plan view of another embodiment of the device of the present invention;

FIG. 23F is a partial plan view of another embodiment of the device of the present invention;

FIG. 26 is a plan view, partially in cross section, of yet another acetabular liner extraction device in accordance with yet another embodiment of the present invention;

FIG. 26A is a partial plan view of the jaws of the device of FIG. 26;

FIG. 26B is a partial plan view of the jaws of yet another device according to the present invention;

FIG. 32 is a flow chart of a method for performing hip arthroplasty in accordance with an embodiment of the present invention; and FIG. 33 is a flow chart of a method for performing hip arthroplasty in accordance with another embodiment of the present invention.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 5:
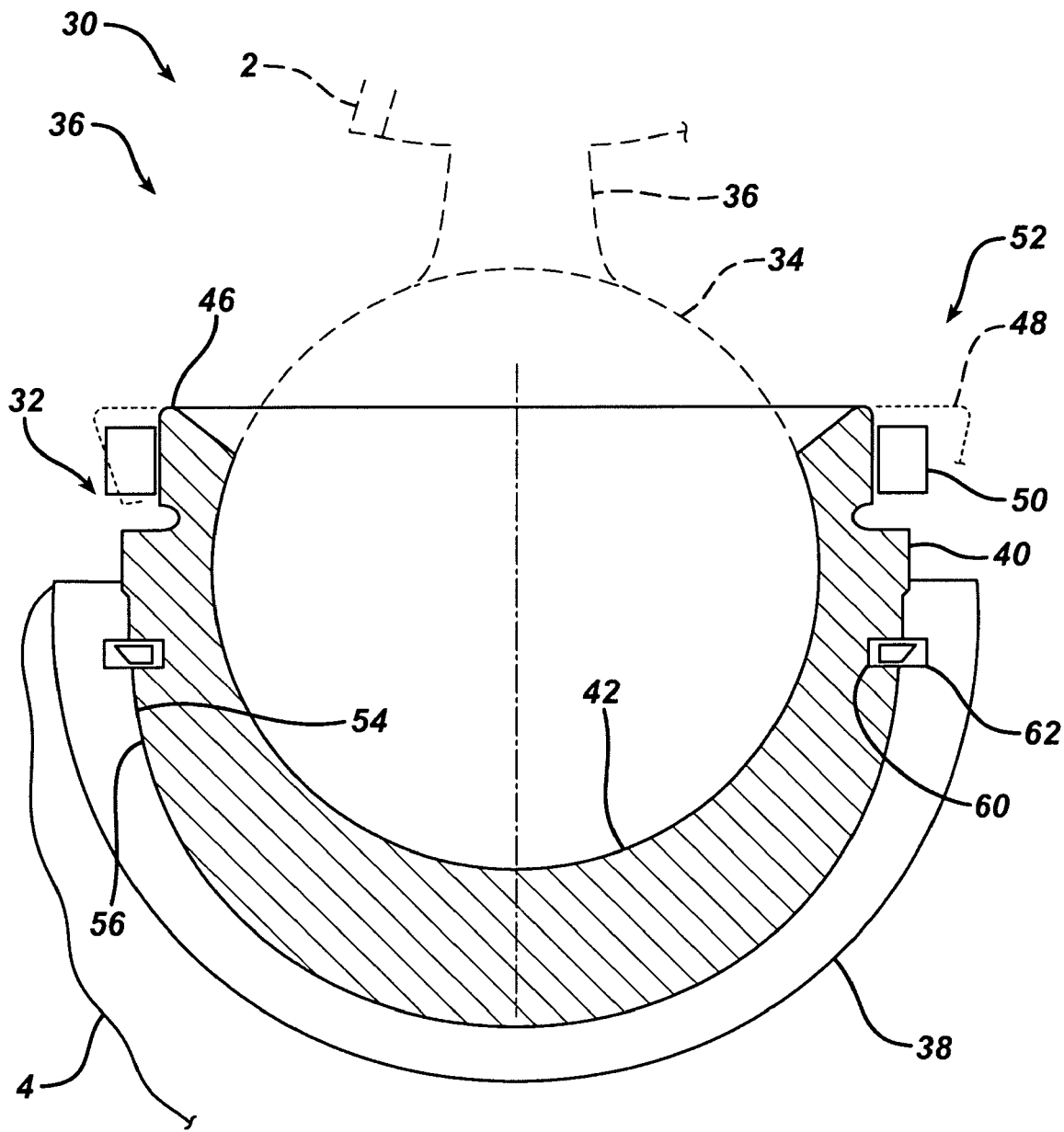
FIG. 5 is a plan view, partially in cross-section, of a constrained hip prosthesis for use with the extraction device of the present invention.

Referring now to FIG. 5, prosthesis 30 is shown for use with the extraction device of the present invention. The hip prosthesis 30 includes an acetabular cup 32, a head 34, connected to the acetabular cup 32, and a stem 36, fixably attached to the head 34. The acetabular cup 32 is fixably secured to acetabulum 4 while the stem 36 is fixably attached to femur 2.

The acetabular cup 32 includes a shell 38, which is fixably attached to the acetabulum 4 and a liner 40, which is secured to the shell 38. The shell 38 may be made of any suitable, durable material and may, for example, be made of a metal, a plastic, or a ceramic material. The liner 40 may be made of any suitable, durable material for example, a metal, a plastic, a ceramic. To conform to the characteristics of human cartilage, the liner 40 may be made of a polymer for example, cross-linked ultra-high molecular weight polyethylene, for example Marathon® as in described in U.S. Pat. No. 6,228,900 to McKellop, et al.

Figure 6:
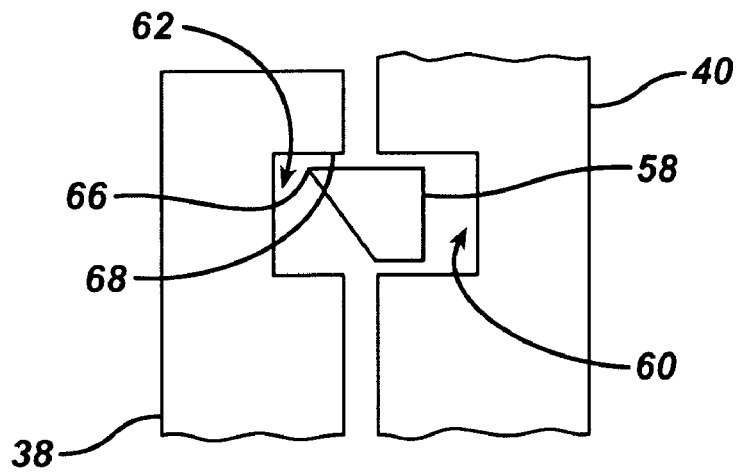
FIG. 6 is a partial view, partially in cross-section of the ring engaged in the prosthesis of FIG. 5.

The acetabular cup 32 of FIG. 6 is utilized as part of a constrained hip prosthesis 30. A constrained prosthesis is utilized to avoid dislocation of a hip joint for a patient. A constrained hip joint, such as a prosthesis 30 includes liner 40 having a hit contact periphery 42 that extents to angle α about spherical head 34. The angle α is greater than 180° so that the head 34 is constrained within the liner 40.

As shown in FIG. 6, the head 34 may be fitted into liner 40 by proving the liner 40 with slits 44 cut through the cross-section of the liner 40. The slit 44 may include a plurality of equally spaced slits. The slits 44 permit the liner 40 to expand from the position 46 in solid as shown to an expanded position 48 as shown in phantom.

When the head 34 is inserted and seated against the liner inner periphery 42, the liner 40 returns back to first position 46. When in first portion 46 band 50 is applied to groove 52 in the liner 40 and the head 34 is contained in the liner 40.

The liner 40 may be secured to shell 38 in any suitable manner. The present invention may be used to remove a liner from a shell independent of the manner, which the liner is secured to the shell. The liner 40 may be secured to the shell 38, for example, in the manner as shown in FIG. 5. The liner 40 may be secured by two distinct connecting mechanisms. For example, and as shown in FIG. 5, the shell 38 may include a tapered inner periphery 54 which mates with tapered external surface 56 of liner 40.

In addition to the taper lock, the hip prosthesis 30 of FIG. 5 may include a split or locking ring 58, which is fitted in liner groove 60 and shell groove 62. The locking ring 58 may be solid or split. The ring 58 is expanded to fit into the liner groove 60, and is compressed into the liner groove 60 so that the locking ring may fit into the inner periphery of the shell and thereby lock into the shell groove 62.

Figure 1:
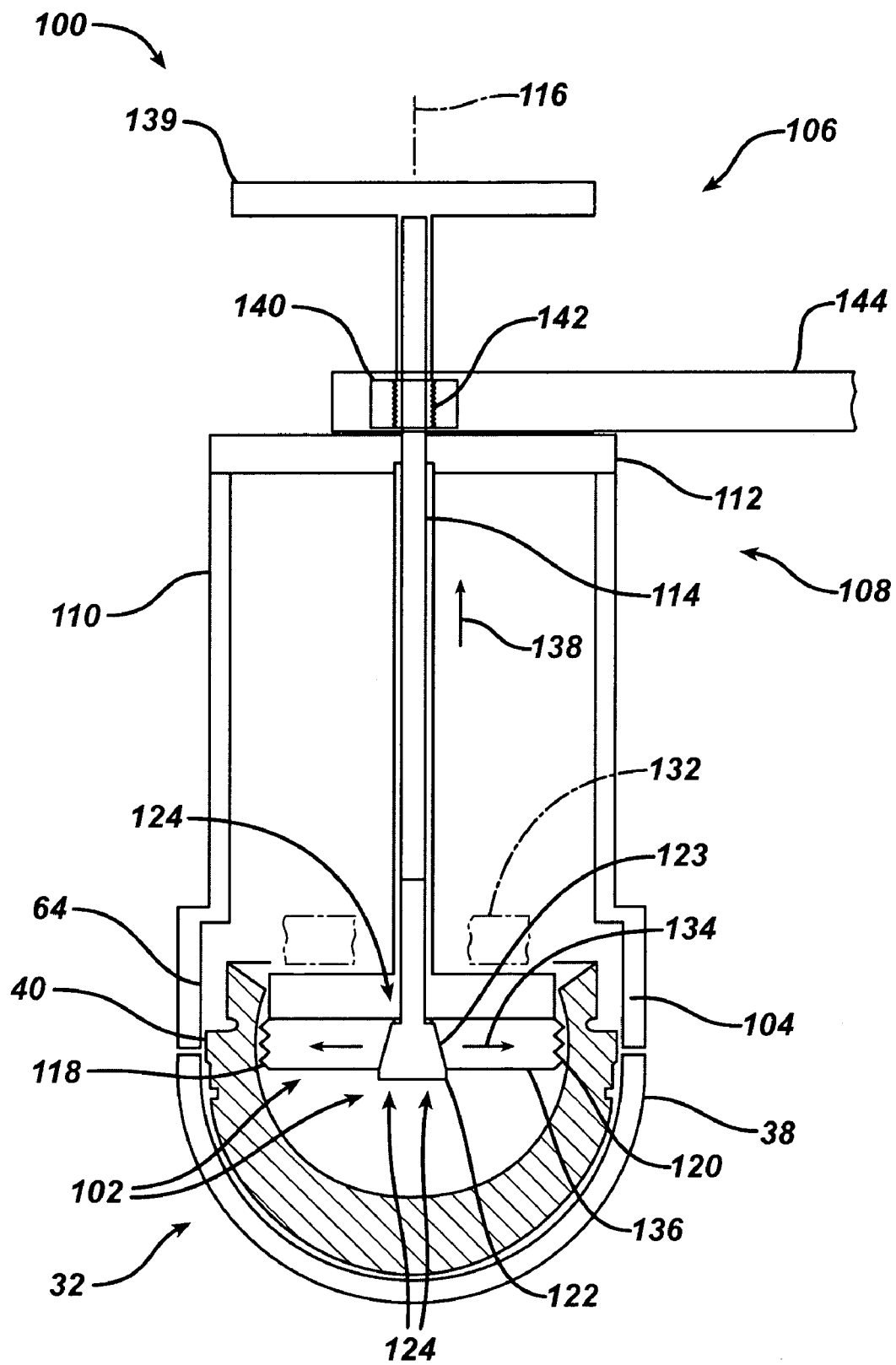
FIG. 1 is a plan view, partially in cross-section, of an acetabular liner extraction device in accordance to the present invention.

According to the present invention and referring now to FIG. 1, extraction device 100, according to the present invention, is shown. The extraction device 100 is utilized for removing the liner from the shell of an acetabular cup. The extraction device 100 includes a jaw 102 for cooperation with the liner 40 of the acetabular cup 32. The jaw 102 includes a portion 104 in the form of, for example, a tip for penetrating into the liner 40. The extractor device 100 further includes a handle 106 operably associated with the jaw 102. The handle 106 is adapted for gripping the extraction device 100.

The extraction device 100 may, for example, include a frame 108 for supporting the handle 106. The frame 108 may include supports 110 for cooperation with distal face 64 of the shell 38. The supports 110 are used to support base 112 of the frame 108. A shaft 114 is rotatably supported along longitudinal axis 116 of the shaft 114.

As shown in FIG. 1, the jaw 102 is connected to the shaft 114. The jaw 102 may, as shown in FIG. 1, include a first jaw segment 118 and a second opposed jaw segment 120. It should be appreciated that a different number of jaws, for example 3 jaws, may be used. The jaw segments 118 and 120 may be penetrated into the liner 40 in any suitable fashion. For example and is shown in FIG. 1, the extraction device 100 further includes an actuator 122.

The actuator 122 is used to actuate or move the jaw segments 118 and 120 into engagement with the liner 40. The extractor 122 as shown in FIG. 1, may be in the form of a tapered component. For example, a conifrustical tapered component. An external taper 123 may cooperate with an internal taper 124 formed from the first jaw component 118 and the second component 120.

Figure 1A:
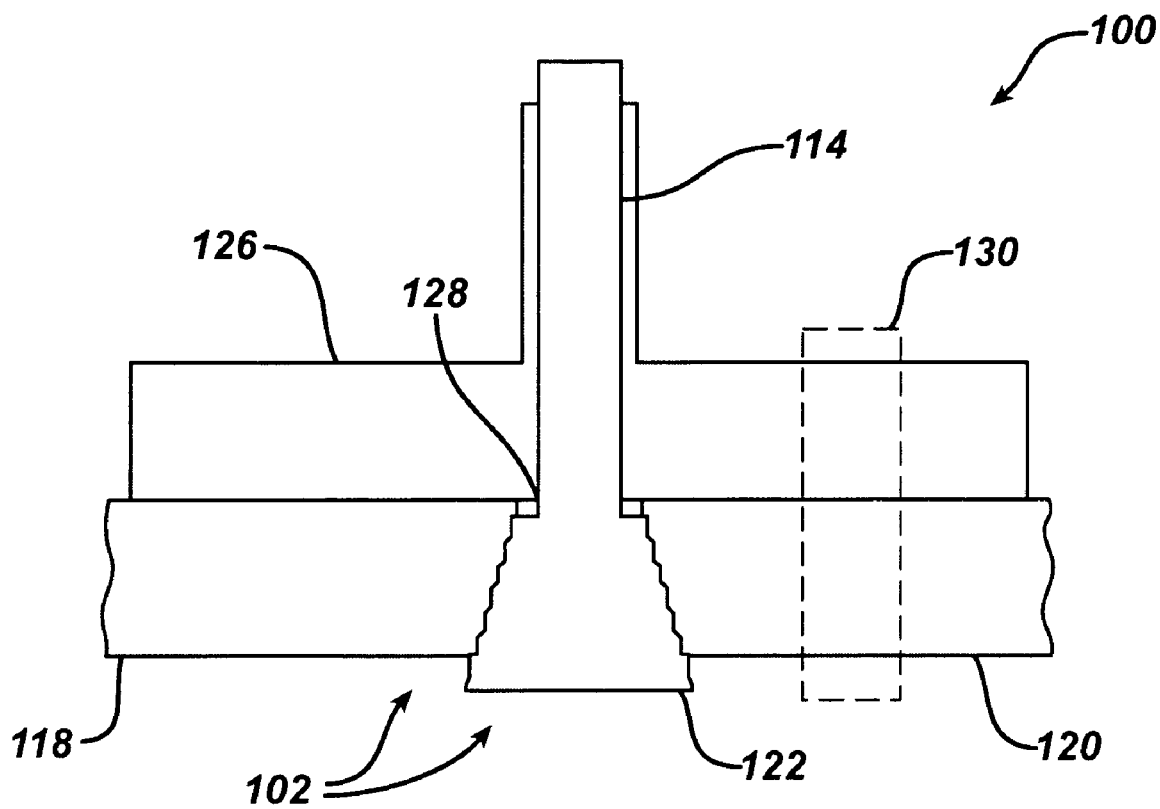
FIG. 1A is a portion plan view of the device of FIG. 1 showing the articulation in greater detail.

Referring now to FIG. 1A, the shaft 114 may include a ring 126 extending from end 128 of the shaft 114. Guiding supports 130 may be connected to the ring 126 and serve to guide and support the first jaw segment 118 and the second jaw segment 120.

Referring again to FIG. 1, the jaw segments 118 and 120 are contracted into the position as shown in phantom as first position 132. In position 132, the jaw segments 118 and 120 may enter the inner portion of the liner 40. After the jaw segments are positioned within the liner 40, the jaw segments 118 and 120 are expanded outwardly in the direction arrows 134 until the jaw segments 118 and 120 engage with the liner 40 in second position 136.

The jaw segments 118 and 120 are advanced to the second position 136 by moving the shaft 114 of the actuator 122 in the direction of arrow 138. The movement of the shaft 114 of the actuator 122 in the direction of arrows 138 results in the first jaw segment 118 and the second jaw segment 120 moving in the direction of arrows 134 to engage with the liner 40. After the jaws are engaged with the liner 40, the shaft 114 continues to be advanced in the direction of arrow 138 until the liner 40 separates from the shell 38.

While it should be appreciated that the shaft 138 may be moved in the direction of arrow 138 simply by pulling upwardly on the t-portion 139 of the handle 106 of the direction of arrow 138. It should be appreciated, however, that the force required to extract the liner 40 may be such that a tool may be required to assist with the extraction device 100.

For example and as shown in FIG. 1, the extraction device 100 may further include a nut 140 threadably secured to external threads 142 formed on the shaft 114. A wrench, for example, torque wrench 144 may be used to advance the nut 140 in the direction opposite the arrow 138 such that the shaft 114 may move in the direction of arrow 138 with respect to the base 112 of the frame 108 of the extraction device 100.

Figure 2:
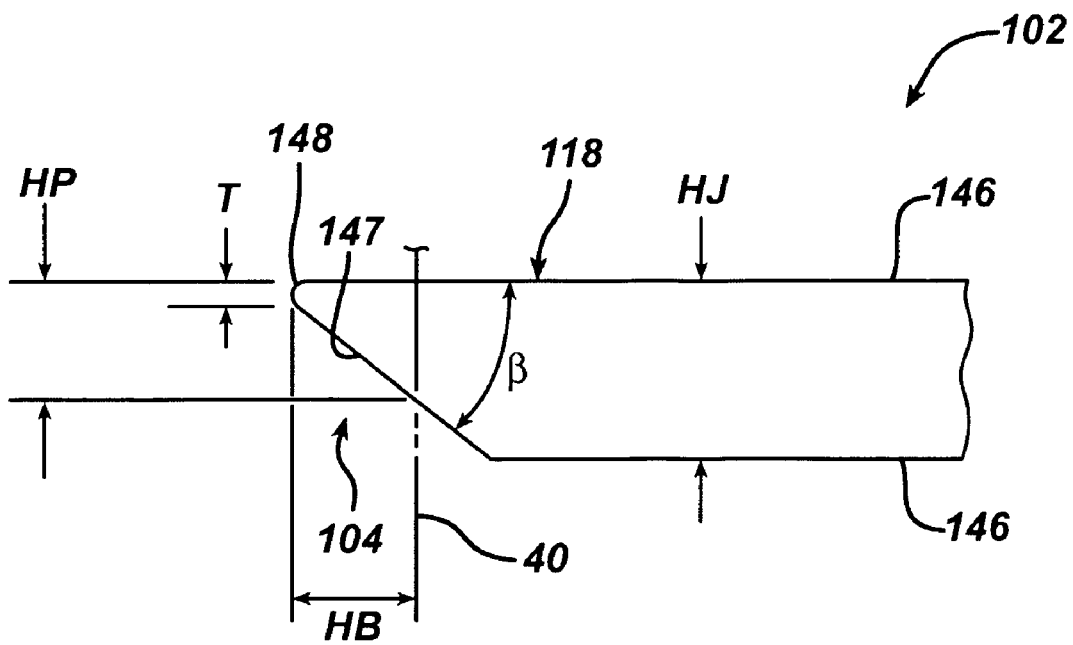
FIG. 2 is a partial plan view of the jaw of the device of FIG. 1'.
Figure 3:
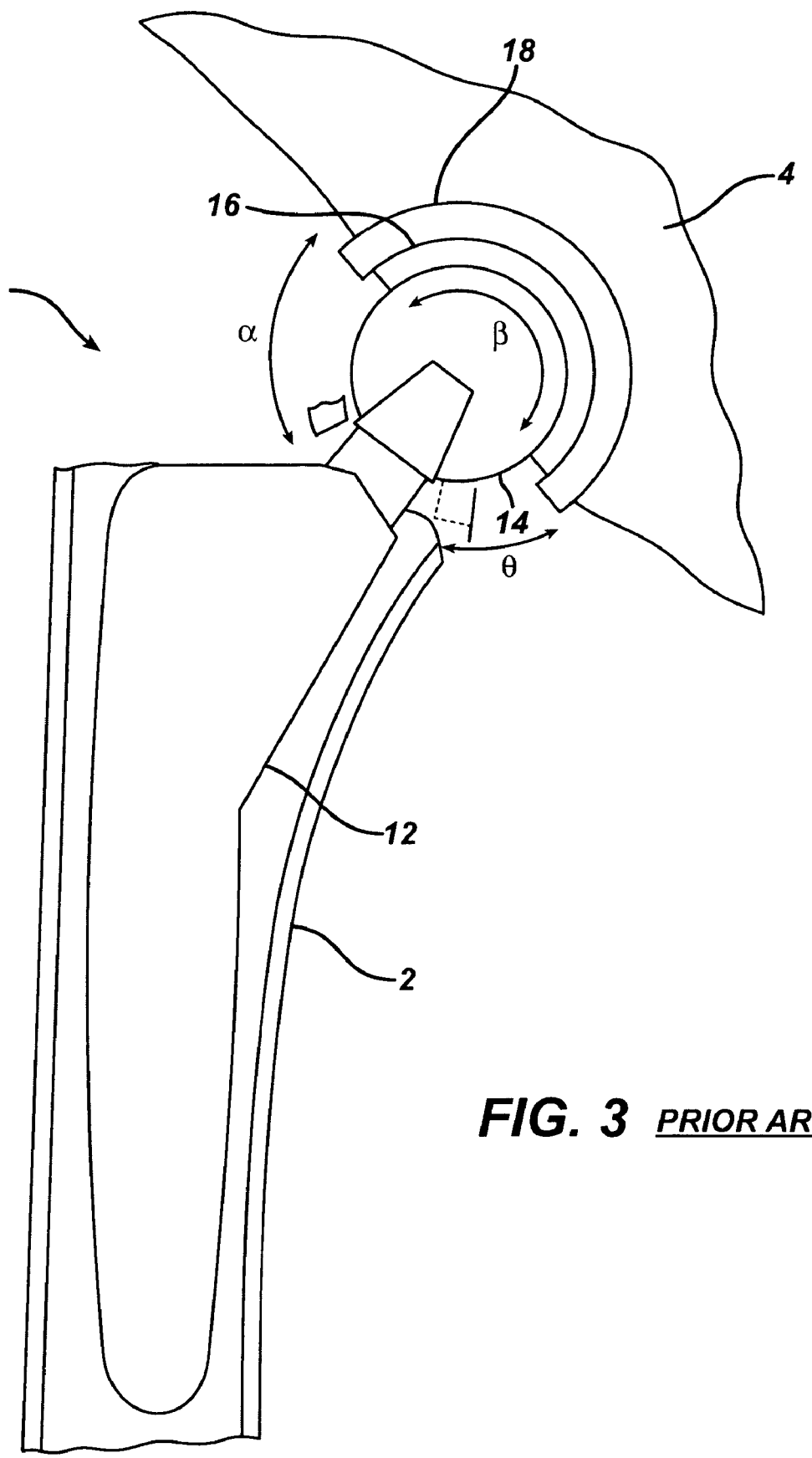
FIG. 3 is a plan view of a prior art unconstrained hip prosthesis.
Figure 4:
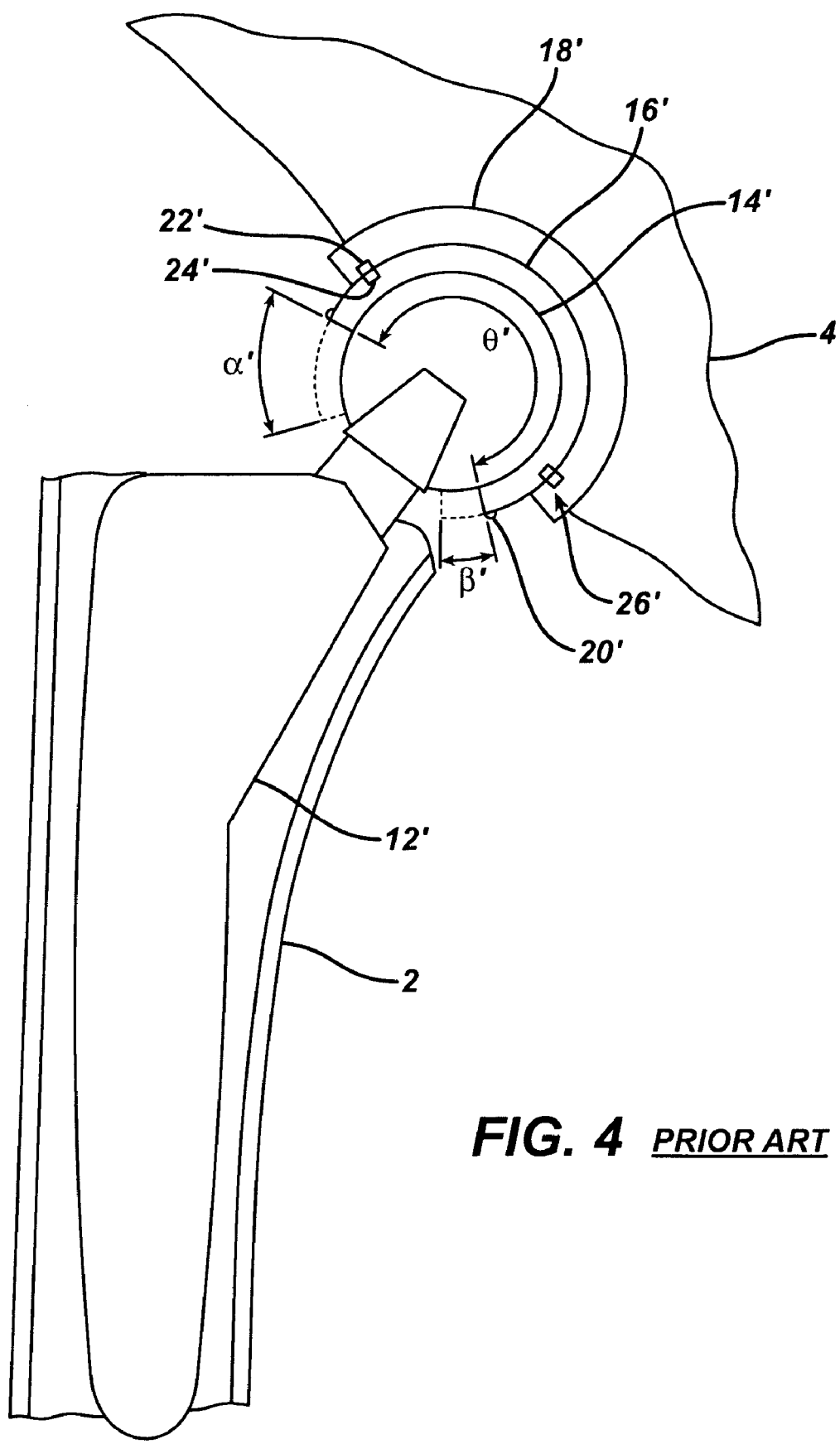
FIG. 4 is a plan view of a prior art constrained hip prosthesis.

Referring now to FIG. 2, one of the jaws 102, for example, first jaw 118 is shown in greater detail. The jaw 118 includes portion 104 for penetrating the liner 40.

As shown in FIG. 2, the first jaw 118 may have any suitable shape. For example and is shown in FIG. 2, the jaw segment 118 may have parallel spaced apart faces 146.

The jaw segment 118 may include the portion 104 for penetrating the liner 40. To penetrate the liner 40, the jaw 118 may include a point or tip 148. The point or tip 148 may be defined by a height or thickness T. The tip 148 may, for example, be perpendicular to the face 146. An included angle $\beta$ may extend from the point 146 to one of the parallel spaces 146 and to angled face 147. The angle $\beta$ may be selected to provide for a sufficient penetration of the liner 40. For example, the angle $\beta$ may be, for example, 5° to 49°.

The parallel surfaces 146 of the jaw segment 118 may be separated by a distance, for example, HJ. The jaw 118 may be designed such that the jaw 118 may penetrate the liner 140 a distance defined by HB or height of the penetration. The distance HB, may be, for example, 10 to 20 mm, while the distance HP, may be, for example, 1 to 8 mm.

Figure 7:
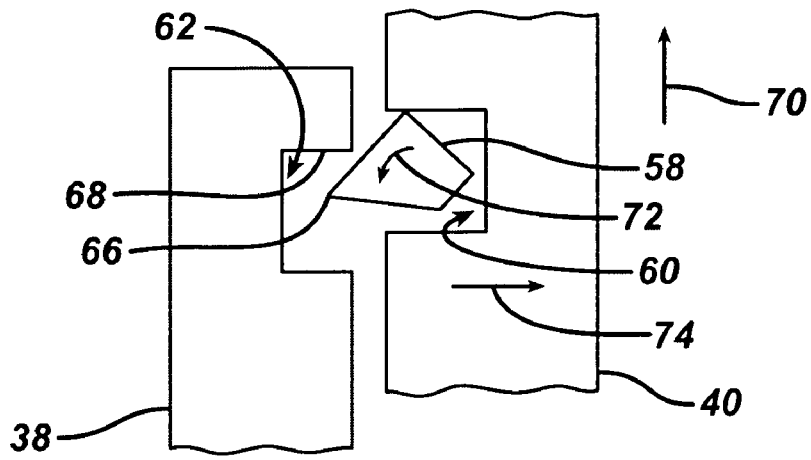
FIG. 7 is a partial plan view, partially in cross-section of the ring of FIG. 6 partially deflected.
Figure 8:
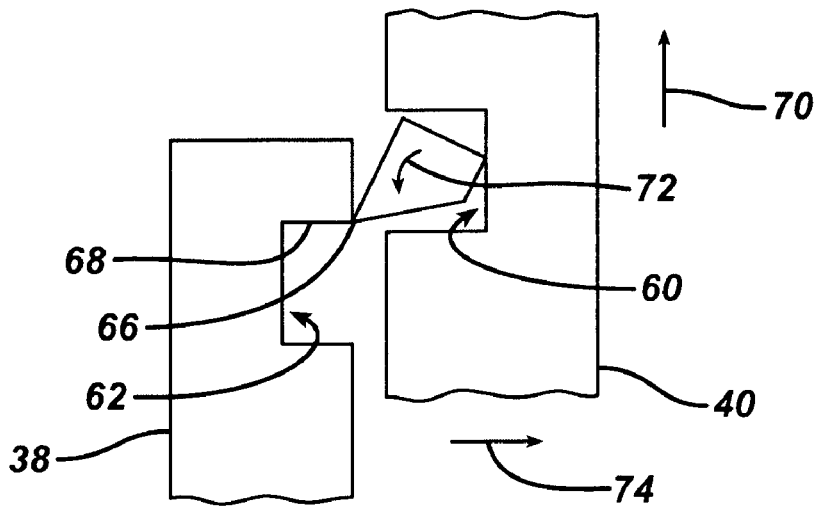
FIG. 8 is a partial plan view, partially in cross-section of the ring of FIG. 6 fully deflected.

Referring now to FIG. 6, 7, and 8 the liner is shown as being pulled from the shell 38 progressively, utilizing the extraction device of the present invention. Referring now to FIG. 6, the locking ring 58 is shown in its installed position within the liner groove 60 and the shell groove 62. The outer edge 66 of the locking ring 58 is shown in position in contact with distal surface 68 of the shell groove 62.

Referring now to FIG. 7, the liner 40 is shown advanced in the direction of arrow 70 with respect to the shell 38. The extracting device of the present invention is used to move the liner 40 in the direction of arrow 70. As the liner 40 is advanced in the direction of arrow 70, outer edge 66 of the locking ring 58 is forced against distal surface 68 of the shell groove 62 causing the locking ring 58 to rotate in the direction of arrow 72.

As the locking ring 58 rotates in the direction of arrow 72, the outer edge 66 of the locking ring 58 moves away from the distal surface 68 of the shell groove 62 and inwardly in the direction of arrow 74. Because the locking ring 58 is split, the locking ring 58 may move in the direction of arrow 74 as the locking ring 58 contacts the distal surface 68 of the shell groove 62.

Referring now to FIG. 8, the liner 40 is shown advanced further in the direction of arrow 70 with respect to the shell 38. The outer edge 66 of the locking edge ring 58 continues to move inwardly in the direction of arrow 74 and continues to rotate in the direction of arrow 72. The outer edge 66 of the locking ring 58 moves to the point that the locking ring edge 66 is sufficiently in the direction of arrow 74 that the liner 40 and the locking ring 58 may be removed from the shell 38.

Referring now to FIGS. 9-15, yet another embodiment of the present invention is shown as extraction device 200. Extraction device 200, like the extraction device 100 of FIG. 1, is utilized for removing, for example, liner 40 from the shell 38 of an acetabular cup 32. The extraction device 200 includes a jaw. For example, first jaw 218. The first jaw 218 cooperates with the liner 40. The first jaw 218 includes a portion 204 for penetrating the liner 40. The extraction device 200 further includes a handle 206, which is associated with the jaw 218. The handle 206 is adapted for gripping the extraction device 200.

Figure 9:
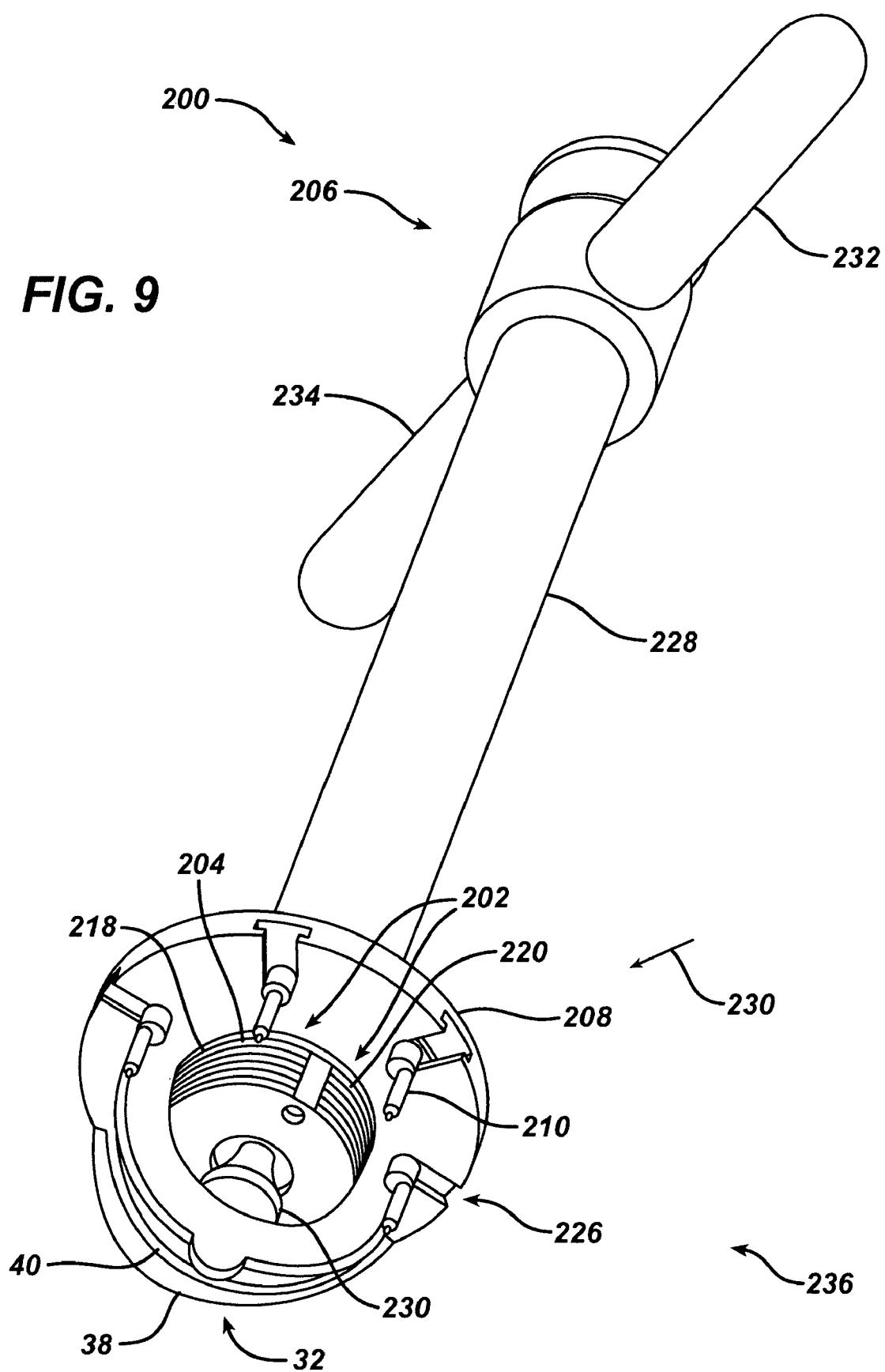
FIG. 9 is a perspective view of an acetabular liner extraction device in accordance with another embodiment of the present invention.
Figure 9A:
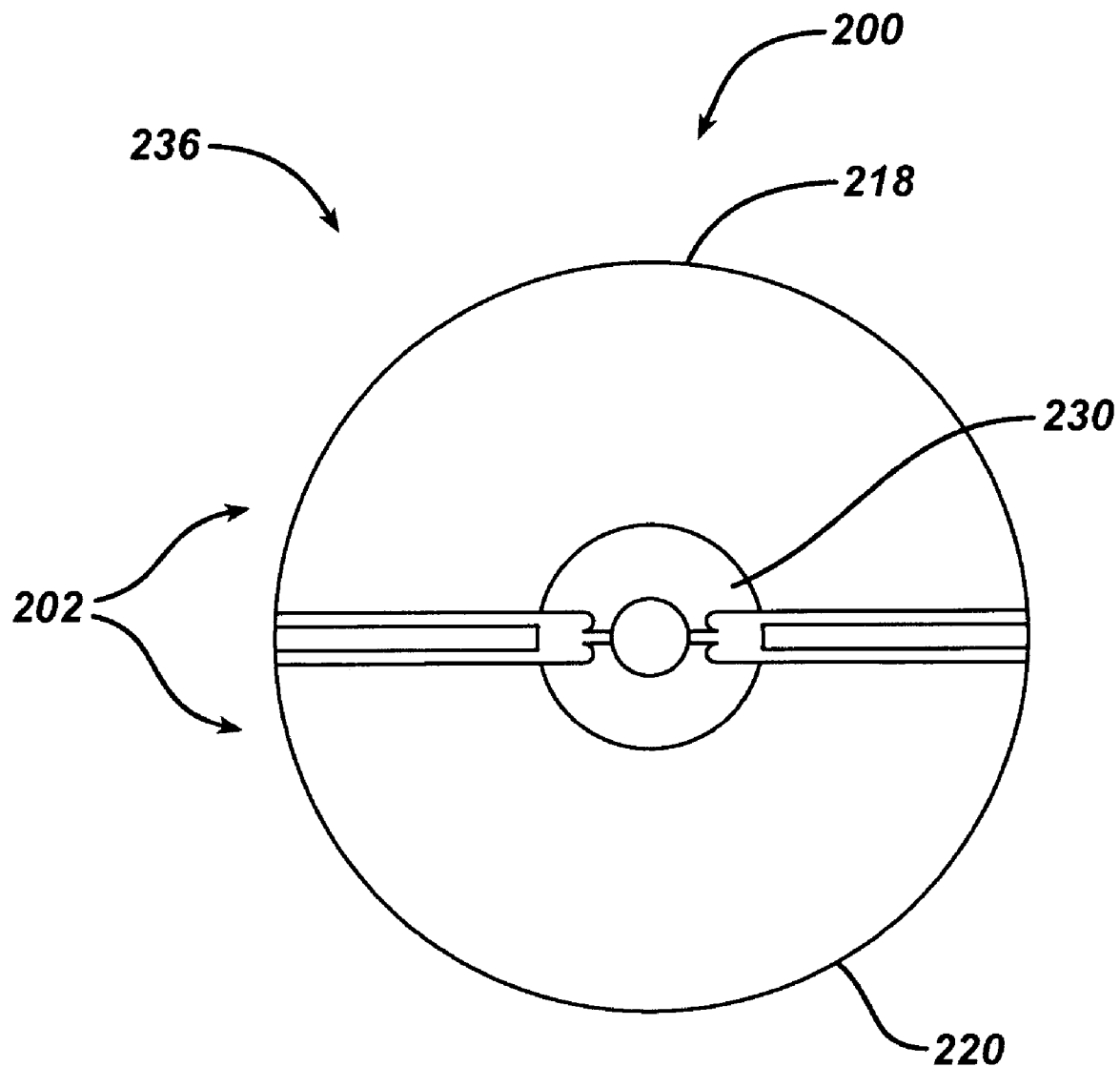
FIG. 9A is a partial bottom view of the device of FIG. 9.
Figure 10:
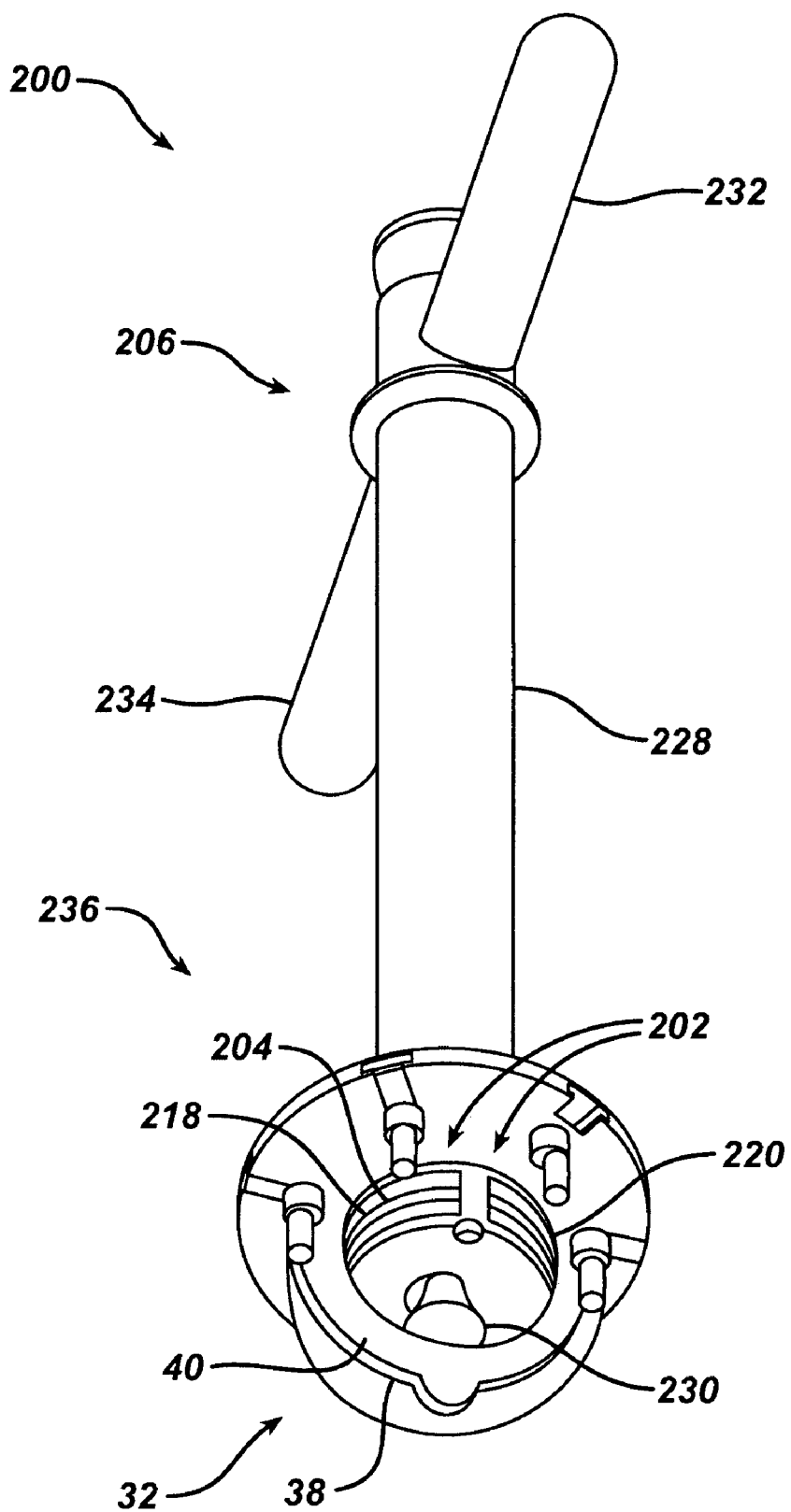
FIG. 10 is another perspective view of the acetabular liner extraction device of FIG. 9.
Figure 11:
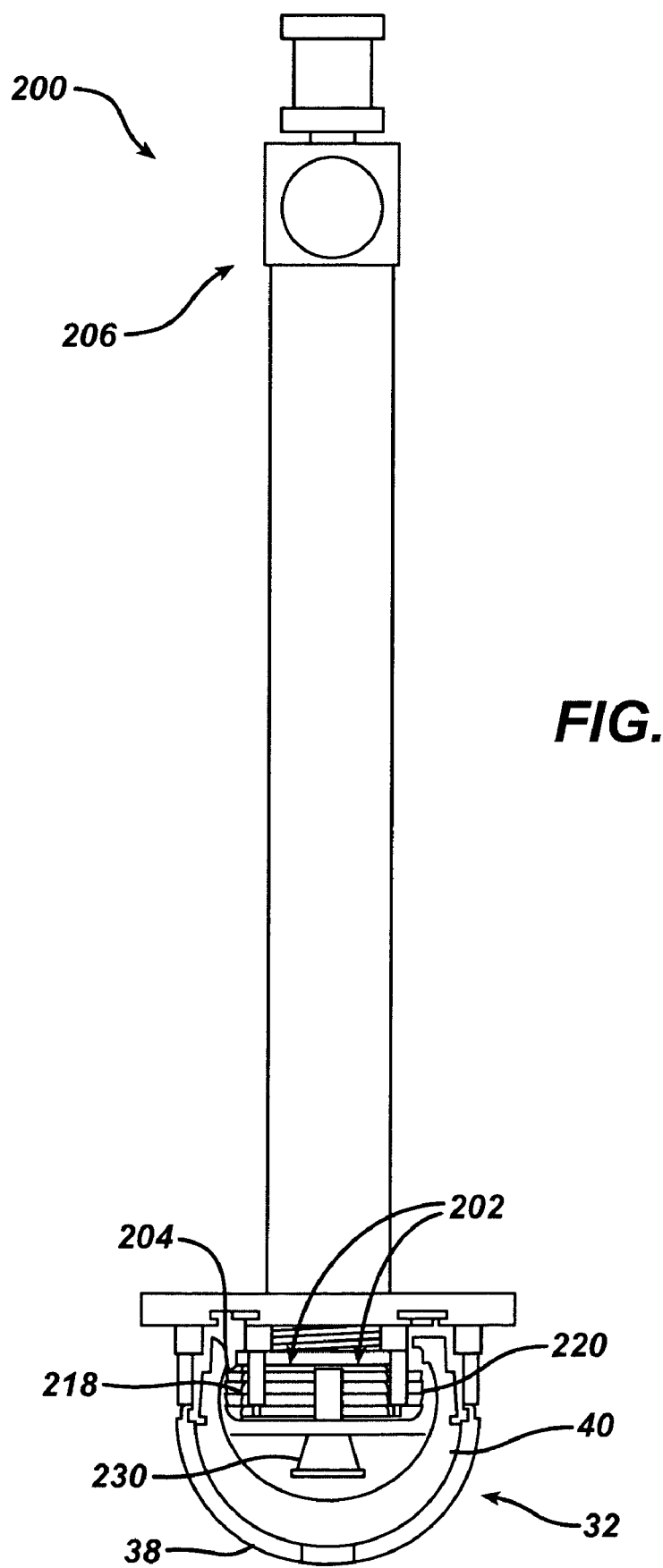
FIG. 11 is a plan view, partially in cross section of the acetabular liner extraction device of FIG. 9.
Figure 12:
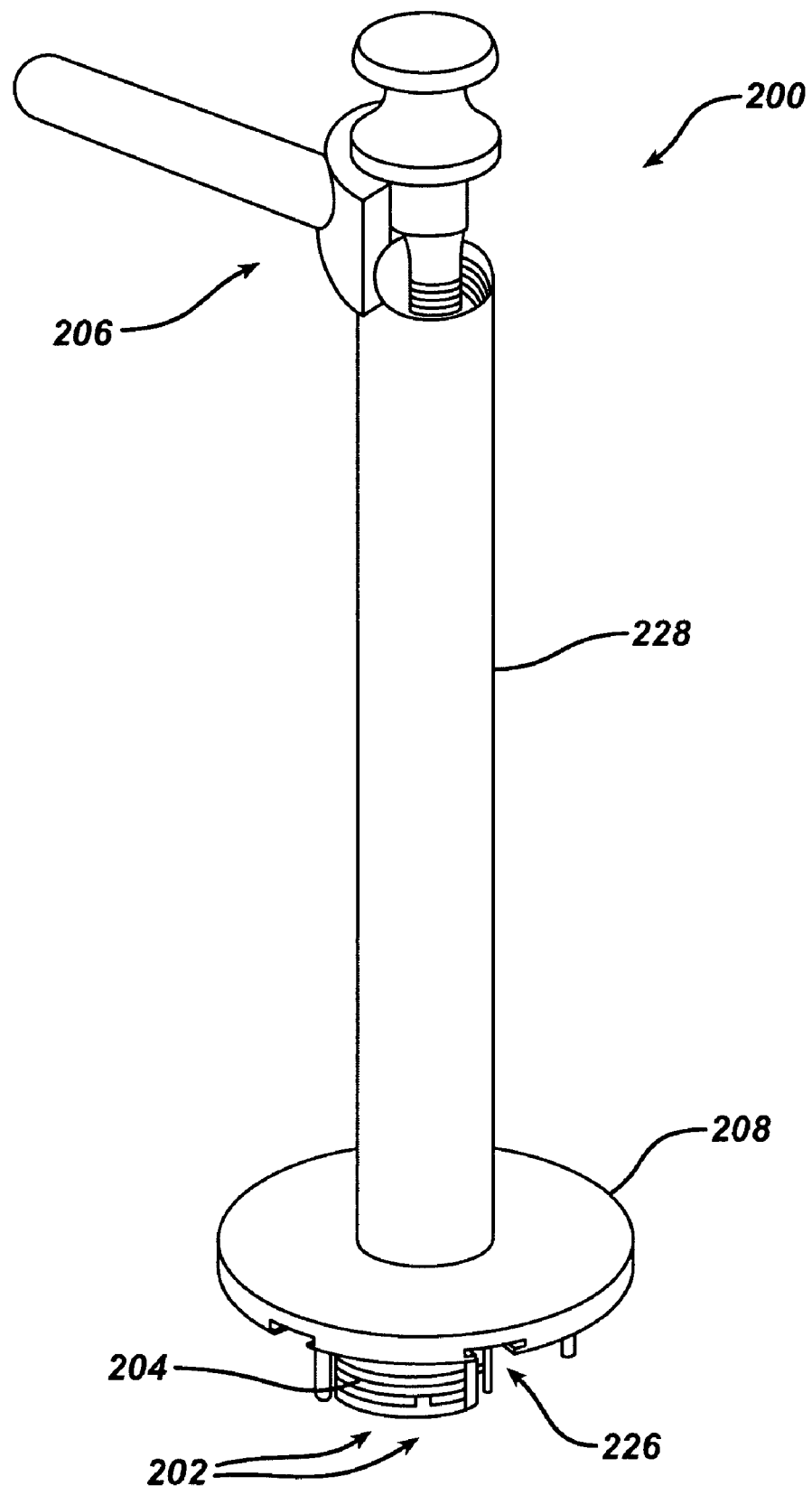
FIG. 12 is another perspective view of the device of FIG. 9.

As shown in FIG. 9, the extraction device 200 includes a base 208. The base 208 serves to support the supports or legs 210. As shown in FIG. 9, a plurality of legs 210 may be used. For example and is shown in FIG. 9, six equally spaced apart legs 210 are used. The legs 210 may, as shown in FIG. 9, be adjustable radially to accommodate different sizes of acetabular cups. For example and is shown in FIG. 9, the base 208 includes a track 226 for permitting the legs to move radially in the direction of arrow 230.

The extraction device 200 further includes a housing 228 for connecting the base 208 to the handle 206. It should be appreciated that the housing 228 may serve as part of the handle 206 as well. The housing 228 may have any suitable shape and may, for simplicity and as shown in FIG. 9, be of a generally hollow or tubular shape having a generally cylindrical outer diameter.

The handle 206 is secured to the housing 228 and may, as shown in FIG. 9, includes a first handle t-portion 232 extending transversally from the housing 204. The handle 206 may likewise have a second handle t-portion 234 of the handle extending transversally from the housing 204 and opposed to the first handle t-portion 232.

The extraction device 200 further includes a jaw assembly 236 for supporting and directing jaws 202 including the first jaw 218 and second jaw 220.

The jaw assembly 236 further includes a protrusion 230 for assisting in actuating the first jaw 218 and the second jaw 220.

Figure 13:
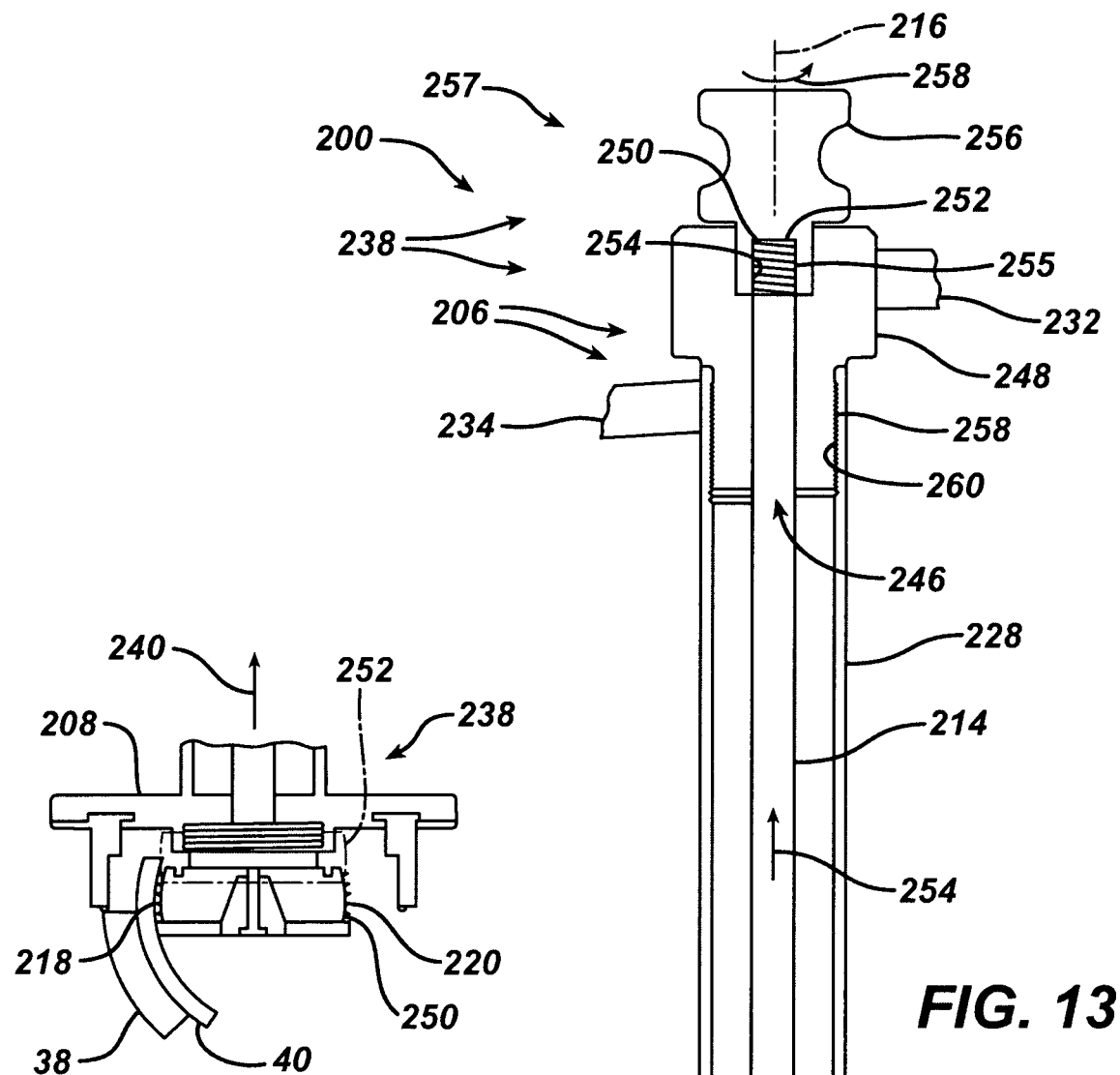
FIG. 13 is a plan view, partially in cross section, of the acetabular liner extraction device of FIG. 9.

Referring now to FIG. 13, jaw actuator 238 of the extraction device 200 is shown. The jaw actuator 238 as shown in FIG. 13, may include the protrusion 230. The protrusion 230 has a generally conifrustical shape and cooperates with tapered cavity 224 formed in jaw assembly 236. The protrusion 230 when advanced in the direction of arrow 240 causes the first jaw 218 and the second jaw 220 to move in the direction of arrows 242 to serve to cause the jaws 218 and 220 to penetrate into the liner 40.

The jaw actuator 238 is used to actuate the jaw or to move the protrusion 230 in the direction of arrow 240. The jaw actuator 238 as shown in FIG. 13, may include a shaft 214 positioned within tubular housing 228. The shaft 214 may move in the direction of arrow 240 with respect to housing 228.

The shaft 218 is connected to the protrusion 230 and is slidably fitted to the base aperture 244 of base 208. The shaft 214 is also slidably fitted within spool aperture 246 of spool 248. The shaft 214 is threadably secured to stem 250 of nut 256 positioned over the end 252 of the shaft 214. Internal threads 254 formed on nut 256 cooperate with external threads 255 formed on shaft 214. The nut 256 is rotatably connected to the spool 248. As the nut 256 is rotated in the direction of arrow 258, the shaft 214 is advanced in the direction of arrow 240 causing the jaws 218 and 220 to penetrate into the liner 40. the jaws first react with the spring until engagement with liner.

Figure 13A:
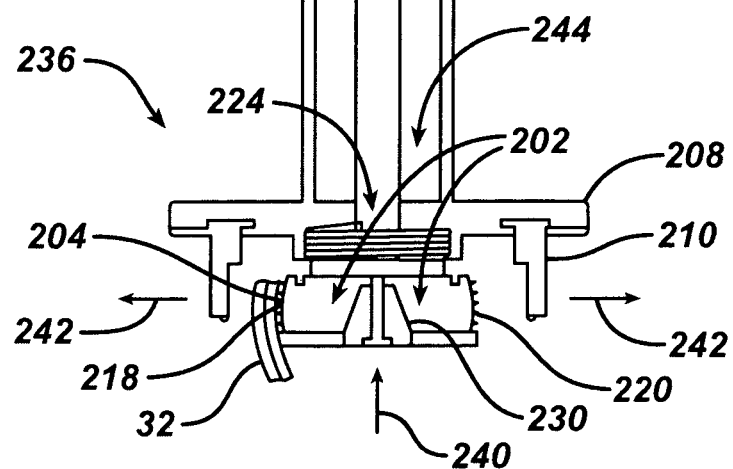
FIG. 13A is a partial plan view, partially in cross-section of FIG. 13.

Referring now to FIG. 13A, once the jaws 218 and 220 are engaged and penetrated into the liner 40 the liner 40 is advanced in the direction of arrow 240. The jaw actuator 238 causes the jaws 218 and 230 to advance in the direction of arrow 240 with respect to the shell 38 and the frame 208. The jaws 218 and 220 thus move from first position 250 as shown in solid to second position 252 as shown in phantom. When the jaws 218 and 220 arrive at the second position 252, as is shown in phantom, the liner 40 has separated from the shell 38.

Referring again to FIG. 13, the jaws 218 and 220 may be advanced in the direction of arrow 240 in any suitable fashion. For example and shown in FIG. 13, the jaw assembly 236 is fixably secured to the shaft 214. The shaft 214 is slidably secured to the base 208 at base aperture 244. The second end 252 of the shaft 214 is connected to the spool 248. As spool 248 is advanced in the direction of arrow 240, the shaft 214 advances, similarly, in the direction of arrow 254.

In order to advance the shaft 214 in the direction of arrow 254 to separate the liner 40 from shell 38, extraction mechanism 257 is used. The extraction mechanism 257 includes a spool 248, which includes external threads 258 formed on a portion thereof. External threads 258 cooperate with internal threads 260 formed on the inner periphery of the tubular housing 228. The spool 248 is thus threadably connected to the tubular housing 228.

The extraction mechanism 257 further includes the first t-portion 232 of the handle 206. The first t-portion 232 is fixably connected and extends transversally from the spool 248. The extractor mechanism 257 further includes the second t-portion 234 of the handle 206. The second t-portion 234 extends transversally from the tubular housing 228.

To actuate the extractor mechanism 257 to separate the liner 40 from the shell 30, the surgeon utilizes one hand to hold the second t-portion 234 of the handle 206 and uses his second hand to grasp the first t-portion 232 of the handle 206. As the surgeon rotates the first handle portion 232 around longitudinal centerline 216, the spool 248 is rotated relative to the tubular housing 228. Since the spool 248 is threadably engaged with the tubular housing 228. As the tubular housing 228 rotates about the longitudinal centerline 216, the spool 248 is advanced in the direction of arrow 240 with respect to the tubular housing 228.

The nut 256 is secured to the spool 248 and causes the nut 256 to likewise advance in the direction of arrow 240. The shaft 214 is threadably secured to the nut 256 such that the nut 256 advances in the direction of arrow 240. The shaft 214, likewise, advances in the direction of 240. As the shaft 214 advances in the direction of arrow 240, the jaws 218 and 220, which are secured to the shaft 214, advance in the direction of arrow 240, removing the liner 40 from the shell 38.

Figure 14:
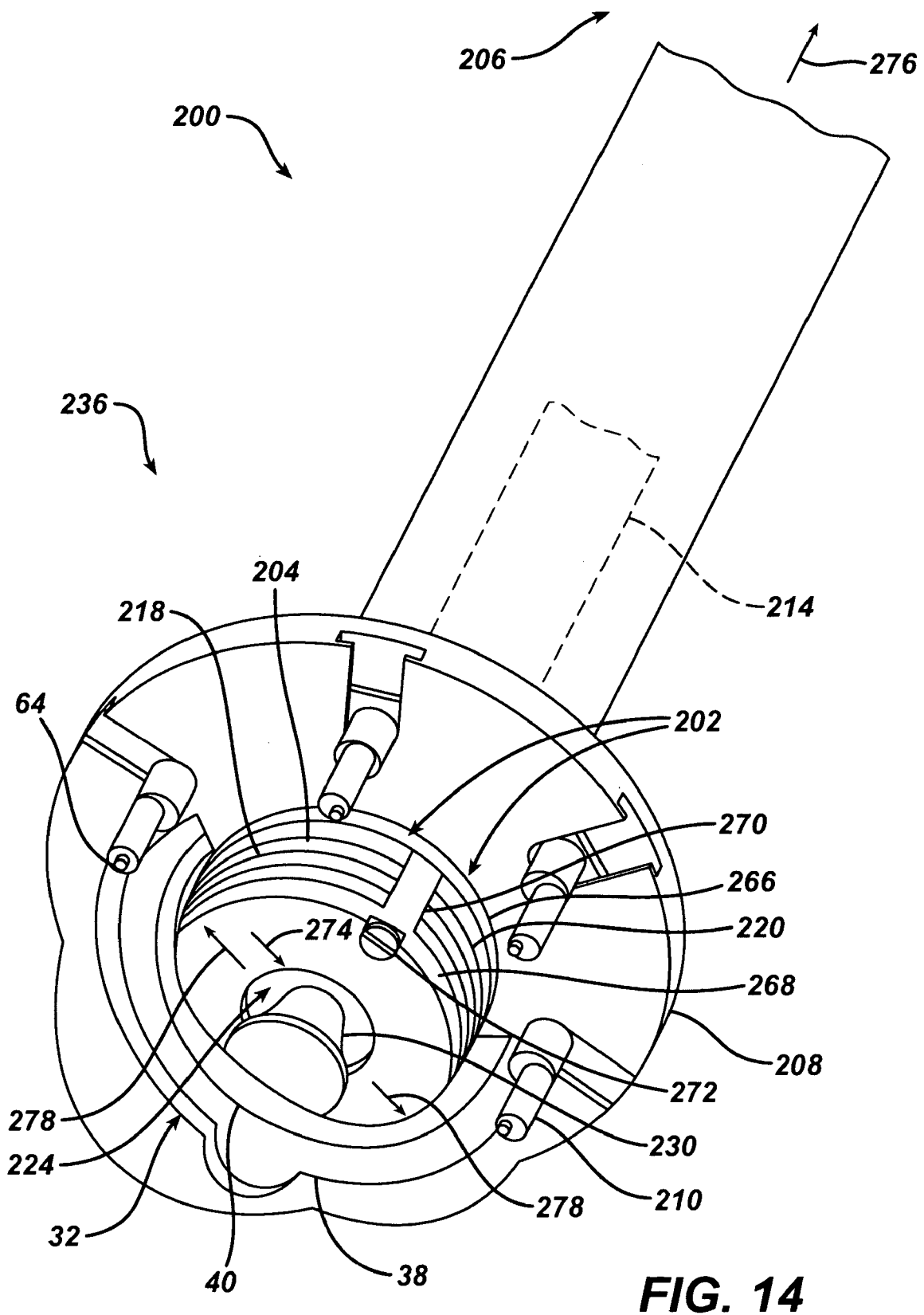
FIG. 14 is a partial perspective view, partially in cross section, of the acetabular liner extraction device of FIG. 9.

Referring now to FIGS. 14 and 15, the jaw assembly 236 for use within the extractor device 200 of the present invention is shown. The jaw assembly 236 is shown in FIG. 14 may include a plurality of jaws, for example, first jaw 218 and second jaw 220. The jaws 218 and 220 are spaced apart and diametrically opposed. The jaws 218 and 220 include a portion 204 of the jaw for penetrating the liner.

Figure 16:
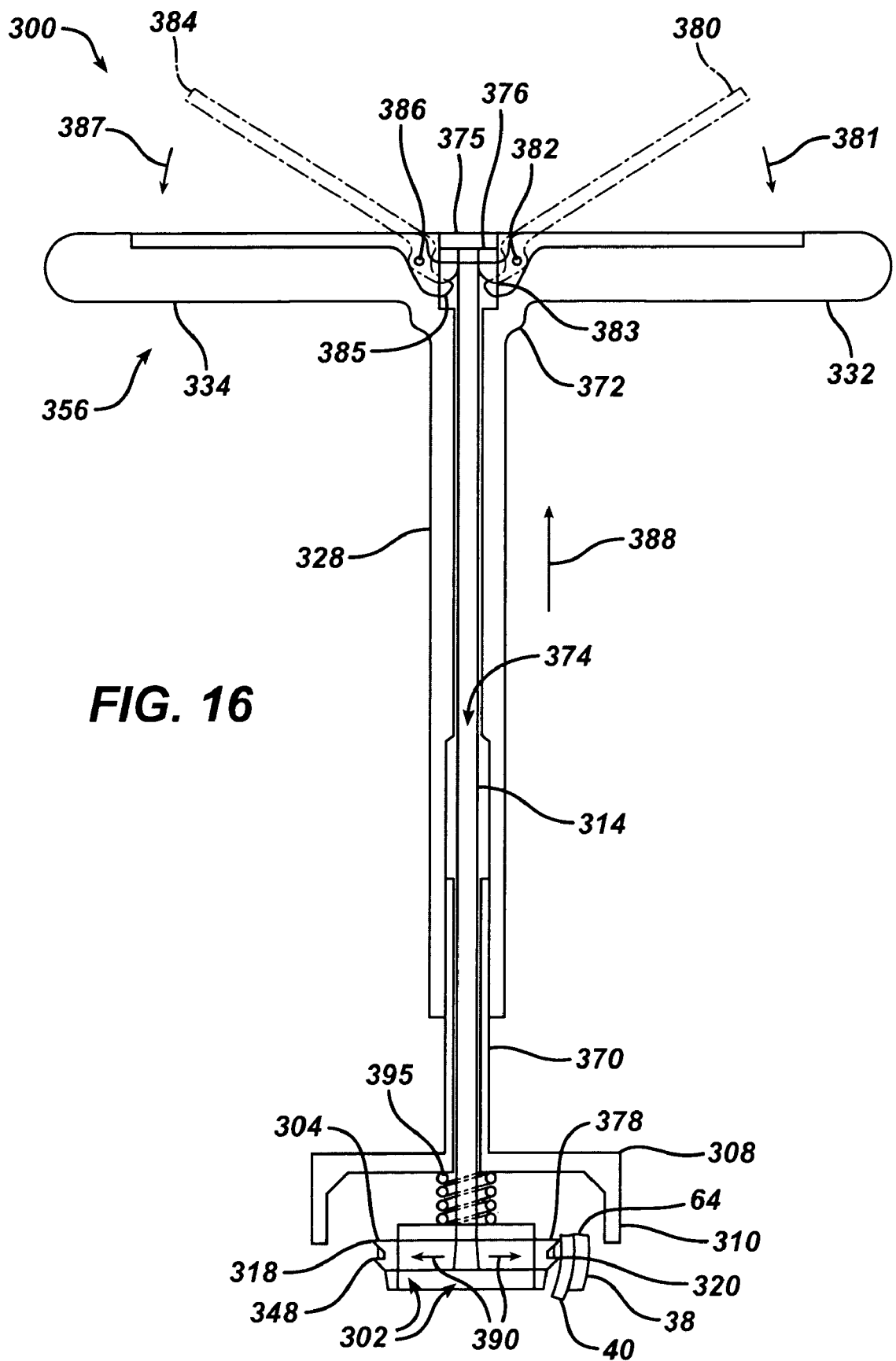
FIG. 16 is a plan view, partially in cross-section of an of an acetabular liner extraction device according to another embodiment of the present invention.

The jaws 218 and 220 as is shown in FIG. 14, are positioned between an inner plate 266 and an outer plate 268. The inner plate 266 and outer plate 268 may have any suitable shape and may, as shown in FIG. 16, be generally cylindrical. The inner plate 266 and outer plate 268 may be parallel to each other and may be spaced apart by columns 270. The columns 270 may be secured to the plates 266 and 268 by fasteners, for example, screws 272. The inner plate 266 may be slidably fitted to the shaft 214. The inner plate 266 and/or the shaft 214 may be slidably fitted to the frame 208.

The shaft 214 may as shown in FIG. 14 be fixably secured to the actuator or conifrustical protrusion 230. The outer plate 268 may include an internal opening 274 to permit clearance of the protrusion 230 therewith. The protrusion 230 cooperates with tapered cavities 224 formed on the first jaw 218 and the second jaw 220. As the shaft 214 moves in the direction of arrow 276, the protrusion 222 likewise moves in the direction of 276 causing the first jaw 218 and the second jaw 220 to move in the direction of arrows 278.

Extraction device 200 may be made of any suitable, durable material capable of sterilization by any commercially available sterilization technique. The extractor device and its components may be made of, for example, plastic, metal, a composite, or a ceramic. The extraction device 200 and its components may be made of a metal. Such metals may include a cobalt chromium alloy, stainless steel alloy, or a titanium alloy.

Referring now to FIGS. 16-23, yet another embodiment of the present invention is shown as extraction device 300. Extraction device 300 of FIGS. 16-23 is similar to the extraction device 200 of FIGS. 13-15, except that the extraction device 300 uses a set of levers to both actuate the jaws and extract the liner from the shell.

For example and is shown in FIG. 16, the extraction device 300 includes an extraction mechanism 356 that is both used to extract the liner from the shell as well as to actuate the jaws. For example and is shown in FIG. 16, the extraction device 300 includes a jaw assembly 336 which cooperates with cup 32 to extract the liner 40 from the shell 38. The jaw assembly 336 is operably connected to the extraction mechanism 356 by an actuator 314 in the form of a shaft.

The extraction device 300 as shown in FIG. 16 includes a base 308 includes a support 310 for supporting face 64 of the shell 38. The base 308 also includes a hollow stem 370 extending in the direction opposed of that the support of 310.

The extraction mechanism 356 further includes a tubular housing 328, which is fittably secured over the periphery of the hollow stem 370 of the base 308. The first t-portion 332 of handle 306 extends transversely from end 372 of the tubular housing 328. A second t-portion 334 extends transversally from end 372 of the tubular housing 328 and is opposed to the first t-portion 332.

The actuator device 300 further includes actuator 314 in the form of a shaft. The actuator 314 slidably fits within central opening 374 of the tubular housing 328. The actuator 314 includes a head 375 located on first end 376 of the actuator 314. The jaw assembly 336 is connected to the actuator 314 at second end 378 of the actuator 314.

The extraction mechanism 356 of the extraction device 300 includes a first lever 380 pivotally connected to handle 306 by first pin 382. Similarly, the extraction mechanism 356 further includes a second lever 384, which is pivotally connected to the handle 306 by second pin 386. As the first lever 380 is rotated in the direction of arrow 381, the first pawl 383 of the first lever 380 advances toward head 375. Similarly, as the second lever 384 is rotated in the direction of arrow 387, the second pawl 385 pushes against head 375. The levers 380 and 384 are rotated in the direction of arrow 381 and 387, respectively to advance pawls 383 and 385 respectively. The pawls 383 and 385 urge the head 385 in the direction of arrow 388 causing the jaws 302 to advance in the direction of arrow 390.

Figure 16B:
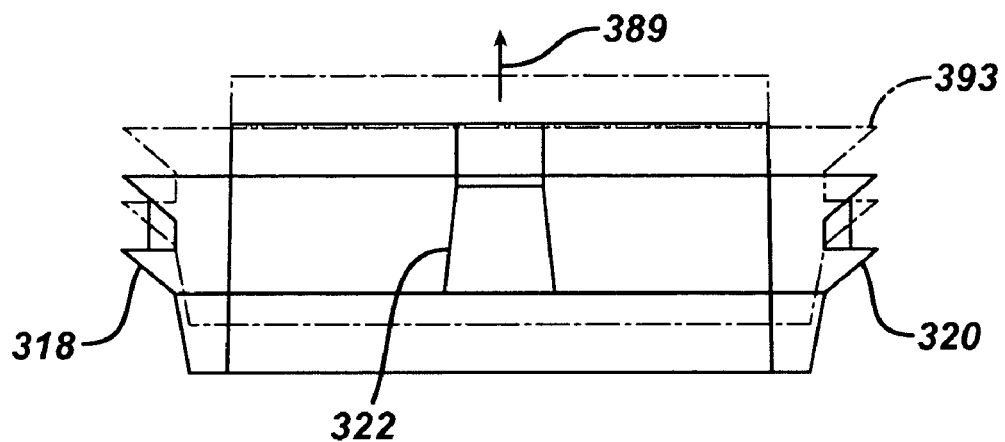
FIG. 16B is a partial plan view of the jaws of the device of FIG. 16.
Figure 16A:
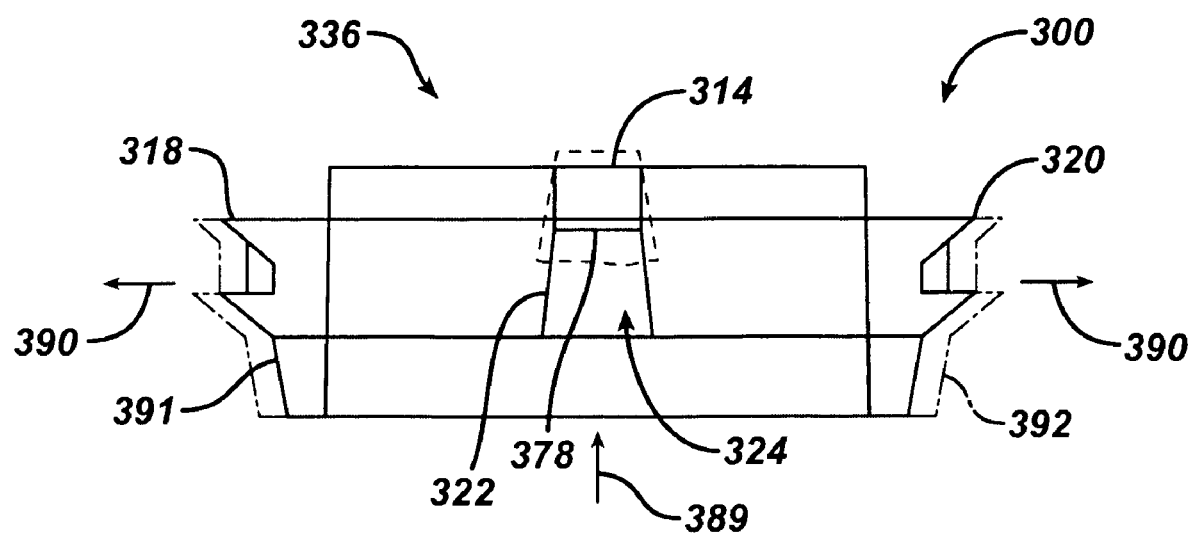
FIG. 16A is a partial plan view, partially in cross-section of the jaws of the acetabular liner extraction device of FIG. 16.

Referring now to FIG. 16A, the jaw assembly 336 is shown in greater detail. The jaw assembly 336 includes a protrusion 322, which is fixably secured to second end 378 of the actuator 314. First jaw 318 and second jaw 320 are positioned transverse and opposed to the protrusion 322. Jaws 318 and 320 define a cavity 324, which cooperates with the protrusion 322 to advance the jaws 318 and 320 in the direction of arrows 390. 16A is missing For example and is shown in FIG. 16A, the jaw assembly 336 defines a first position 391 in which the jaws are in their innermost or closest position to each other. At this position the extraction device 300 may be loaded into the acetabular cup 32. After the extraction device 300 is installed in the acetabular cup 32 the first jaw 318 and the second jaw 320 are advanced into engagement with the liner 40 of the cup 32. By advancing the protrusion 322 in the direction of arrow 389, the protrusion moves from first position 391 to second position 392 as shown in phantom. In position 392, the jaws 318 and 320 are fully engaged with the liner 318.

Referring now to FIG. 16B, after the jaws 318 and 320 are fully engaged with the liner 40, the protrusion 322 is advanced further in the direction of arrow 389 until the protrusion 322 is advanced to third position 393. At position 393, the liner 40 has been separated from the shell 38 and the extraction device may along with the liner 40 may be removed from the shell 38 to complete the extraction of liner 40 from the shell 38.

Figure 17:
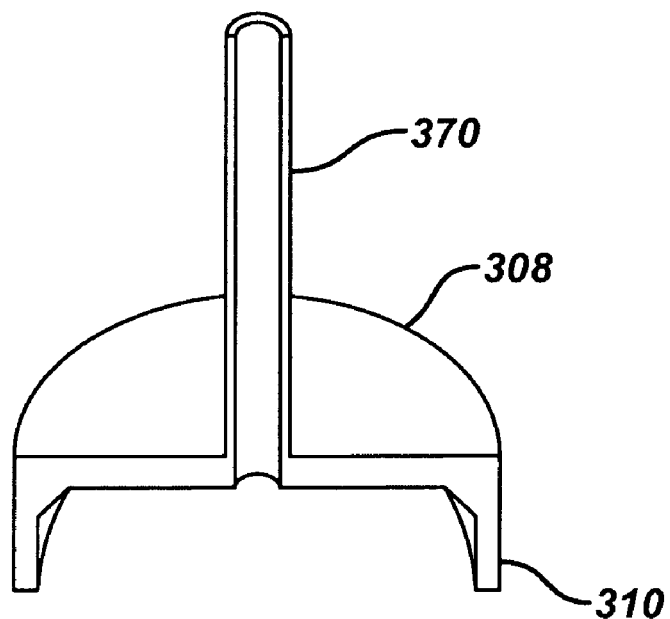
FIG. 17 is a perspective view of the shell support portion of the acetabular liner extraction device of FIG. 16.
Figure 18:
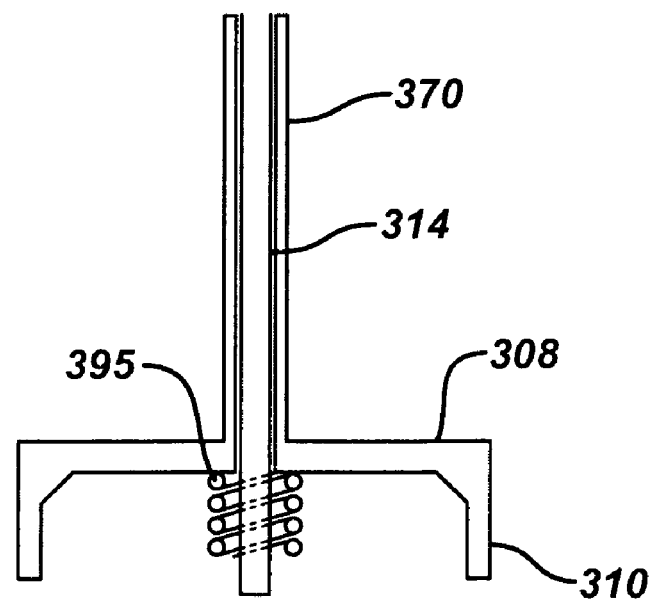
FIG. 18 is a plan view, partially in cross-section of the shell support portion of FIG. 17 of the acetabular liner extraction device of FIG. 16.

Referring now to FIGS. 17 and 18, the hollow stem 370 and the bore 308 may be integral with each other. The bore 308 may be generally disc shaped with a hollow cylindrical support 310 extending from the bore 308. A spring 395 may be positioned below the bore 308 and contained by the shaft 314. The spring 395 is used to urge the jaw assembly 338 in a direction away from base 308.

Figure 19:
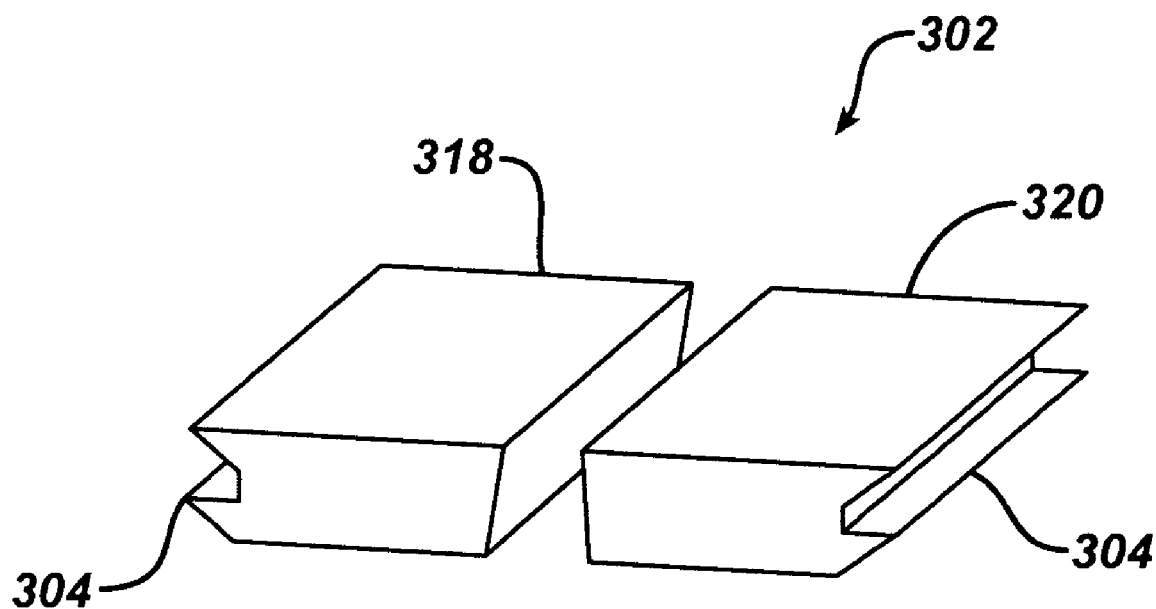
FIG. 19 is a perspective view of the jaws for use with the device of FIG. 16.
Figure 20:
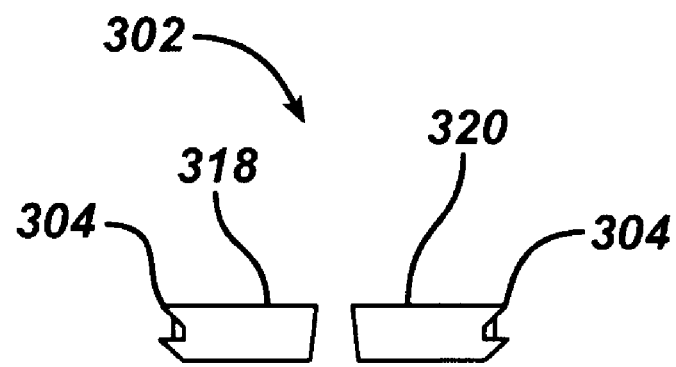
FIG. 20 is a plan view of the jaw of FIG. 19.

Referring now to FIGS. 19 and 20, the jaws 318 and 320 may be generally rectangular with a portion 304, which is defined by a radius and is adapted for penetrations into the liner 40.

Figure 21:
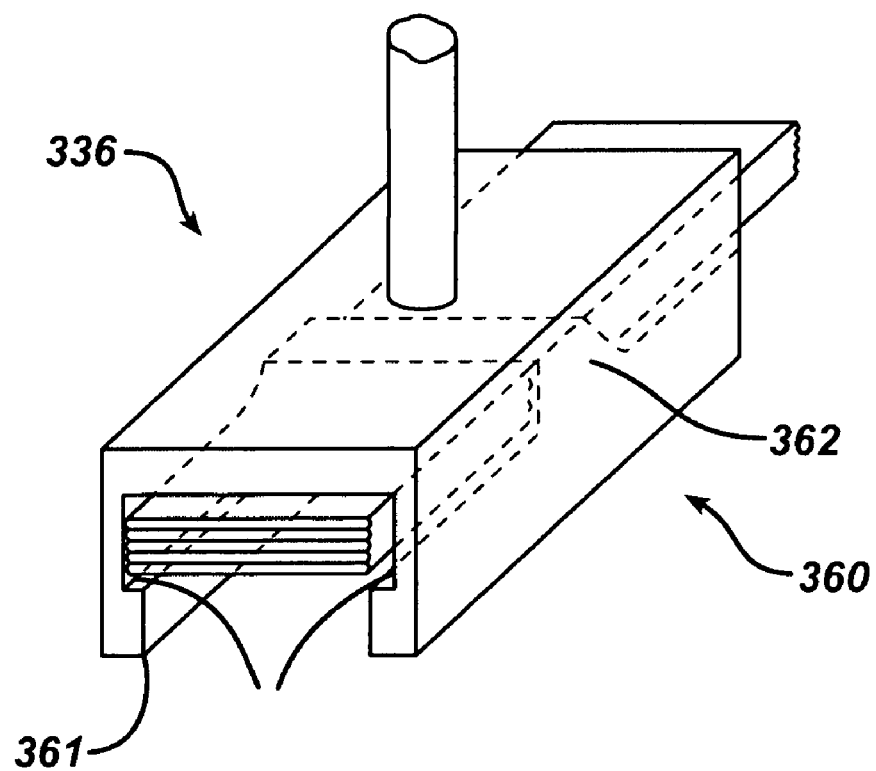
FIG. 21 is a perspective view of the jaw cradle of the device of FIG. 16.
Figure 22:
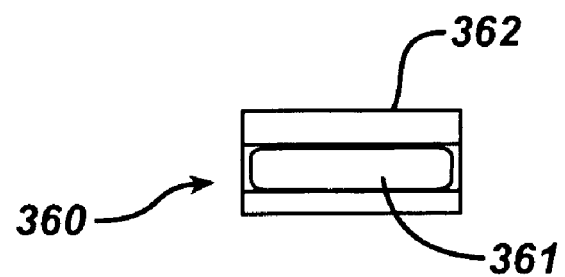
FIG. 22 is an end view of the jaw cradle of the device of FIG. 16.

Referring now to FIGS. 21 and 22, the jaws assembly 336 is shown in greater detail. The jaw assembly 336 includes jaw cradle 360, which includes jaw cradle bottom 361, which is fixably attached to the shaft 314. The jaw cradle 360 further includes the jaw cradle top 362. The jaw cradle bottom 361 is slidably fitted within the inner walls 363 of the jaw cradle top 362. The jaw cradle bottom 361 is partially aligned by a slidable fit of the shaft 314 to the jaw cradle top 362.

Figure 23:
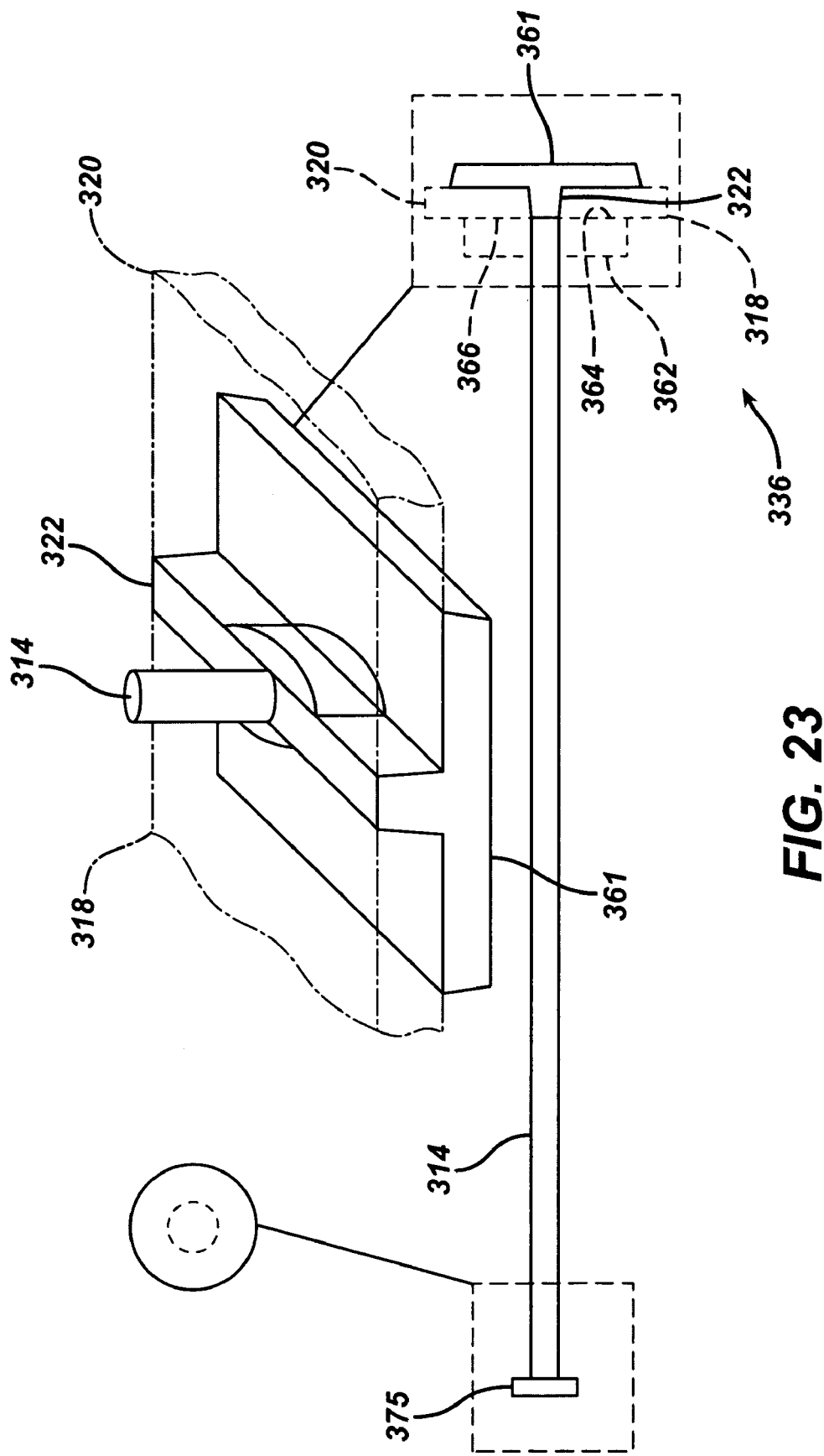
FIG. 23 is a graphic model of the device of FIG. 16.

Referring now to FIG. 23, the jaw assembly 336 is shown with the actuator 314 in symbolic black form. The actuator 314 is fixably secured to the jaw cradle bottom 361 or may be integral therewith.

The first jaw 318 is contacted between the cradle top 362 and the cradle bottom 361. Similarly, the second jaw 320 is cradled between the cradle top 362 and the cradle bottom 361. The first jaw 318 includes an incline surface 364 for cooperation with protrusion 322 of the jaw cradle bottom 361. Similarly, the second jaw 320 includes an incline surface 366 for cooperation with the protrusion 322. As shown in FIG. 23, the first jaw 318 as well as the second jaw 314 may be generally in the form of a rectangular solid.

It should be appreciated, however, that the jaws for the extraction device of the present invention may have other shapes, particularly shapes more in conformance with the hemispherical shape of a typical liner. For example and is shown in FIG. 23A, the jaws 318A and 320A may be in the form of a semi-cylinder. For example, the jaw 318A may include a planar face 370A while the second jaw 320A may include a planar face 371A, which mates against the planar surface 370A of the first jaw 318A to mate with a generally cylindrically shaped pair of jaws. The jaws 318A and 320A combine to define a radius RC and a length LC.

The jaws for an extraction device of the present invention may likewise be that of a truncated sphere. Perhaps the truncated sphere may be truncated at the opposing poles of the sphere. For example and as shown in FIG. 23B, the extraction device may include a first jaw 318B and a second jaw 320B. Again, the first jaw 318B may include a planar face 370B, which mates with planar face 371B of the second jaw 320B.

The first and the second jaw, 318B and 320B, combine to form a truncated sphere defined by a radius RS and a height HS.

The extraction device of the present invention may use a number of alternate structures to actuate the opposed jaws into engagement with the liner. For example, and referring now to FIG. 23C, another embodiment of the present invention is shown as extraction device 300C in which the opposing jaws 318C and 320C are operably connected by a series of two levers 340C and 342C. The forces applied between the adjacent levers 340C and 342C such that the jaws 318C and 320C are moved in opposed directions to engage in the liner 40.

Yet another embodiment of the present invention in FIG. 23D is shown as extracting device 300 that utilizes yet another mechanism for advancing the jaws into the liner. For example and is shown in FIG. 23D, mechanism 356D is in the form of a scotch yoke-type mechanism in which the first jaw 318D and the second jaw 320D include elongated slots 350D diagonally placed on the jaws 318D and 320D. An actuator including a series of pins 352D cooperate with the slots 350D to advance the jaws 318D and 320D in opposed directions to engage into the liner 40.

Referring now to FIG. 23E, another embodiment of the present invention is shown as extraction device 300E. The device 300E includes mechanism 356E in the form of cam 322E that rotatably advances jaws 318E and 320F to engage liner 40.

Referring now to FIG. 23F, yet another embodiment of the present invention is shown as extraction device 300F. The device 300F includes rack and pinion mechanism 356F including a first rack 322F formed on first jaw 318F and a second rack 323F formed on a second jaw 320F. The jaws 318F and 320F are actuated by pinion 325F extending from shaft 314F and cooperating with the racks 322F and 323F to advance jaws 318F and 320F to engage liner 40.

Figure 25:
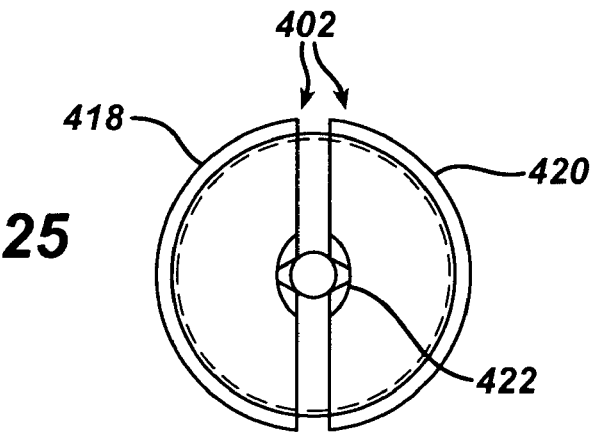
FIG. 25 is a bottom view of the jaws of the acetabular liner extraction device of FIG. 15.

Referring now to FIGS. 25 and 26, another embodiment of the present invention is shown as extraction device 400.

The extraction device 400 is different than the extraction device 300 of FIG. 16 or the extraction device 200 of FIG. 13. The extraction device 400 includes an extraction mechanism 456 different than the extraction mechanism 256 of the extraction device 200 of FIG. 13. The device 400 includes a jaw actuator 438 different than the jaw actuator 238 of the extraction device 200 of FIG. 13.

The extraction mechanism 456 of the extraction device 400 utilizes an extraction cam 475 while the jaw actuator 438 utilizes an actuator cam 422. The actuator cam 422 and extraction cam 475 represent different mechanisms to extract and to actuate than the previous identified extraction devices of the present invention.

Figure 24:
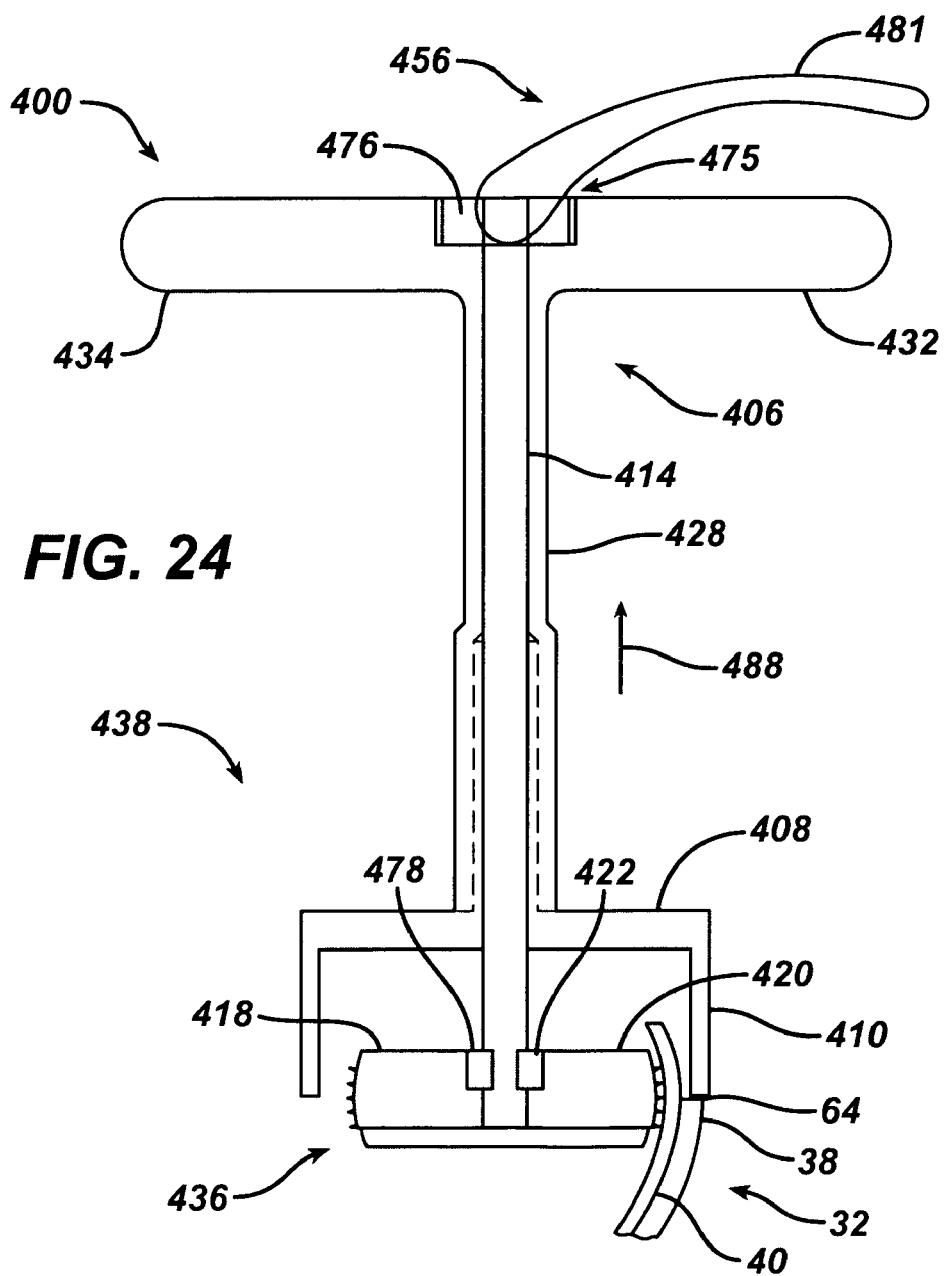
FIG. 24 is a plan view, partially in cross-section, of another acetabular liner extraction device in accordance with another embodiment of the present invention.

Continuing to refer to FIG. 24, the extraction device 400 is described in greater detail. The extraction device 400 includes a base 408. A support 410 extends from the base 408. The support 410 is utilized to support shell 38 of the hip cup 32 at shell face 64. Tubular housing 428 extends from base 408 in a direction opposed to support 410.

A handle 406 extends from housing 428 or may be integral with the tubular housing 428. The handle 406 includes a transverse first t-portion 432 extending transversally from the tubular housing 428. The handle 406 further includes a transverse second t-portion 434 extending transversally from the tubular housing 428 and opposed to the first t-portion 432. An actuator or shaft 414 is slidably and rotatably fitted within the tubular housing 428.

The extractor device 400 further includes the lever 484 connected to first end 476 of the shaft 414. The extractor device 400 further includes the cam 422 connected to second end 478 of the shaft 414.

The extractor device 400 further includes a jaw assembly 436 operably connected to the cam 422 of the shaft 414. The jaw assembly 436 includes first jaw 418 and second jaw 420. The jaws 418 and 420 are used to cooperate with liner 40 of the hip cup 32.

Referring now to FIG. 26, the jaw actuator 438 of the extraction device 400 is shown in greater detail. The jaw actuator 438 includes a jaw assembly 436. The jaw assembly 436 includes the first jaw 418 and the second jaw 420. The jaws 418 and 420 include an arcuate inner periphery 421, which cooperates with cam 422 mounted on shaft 414. As the shaft 414 rotates in the direction of arrow 486, the cam 422, which is mounted to the shaft 414, likewise rotates in the direction of arrow 486. The rotation of the cam 422 in the direction of arrow 486, because of the connection of the cam 422 to the jaws 418 and 420, causes the first jaw 418 and the second jaw 420 to advance in the direction of arrows 471 into contact with liner 40 of the acetabular cup 32.

Continuing to refer to FIG. 26, the extraction mechanism 456 is shown in greater detail. The extraction mechanism 456 is utilized not only to extract the liner 40 from shell 38, but is also used to transmit force to the jaw actuator 438. For example and is shown in FIG. 26, the extraction mechanism 456 includes lever 484 which is pivotally connected to shaft 414 by pin 482. Handle 406 includes a recess 407 about which cam 475 of the lever 484 may rotate about longitudinal axis 473 of the shaft 414.

As shown in FIG. 26, the cam 475 may be integral with the lever 484. The cam 475 is, as shown in FIG. 26, an eccentric cam. For example, the cam 475 defines a cam centerline 477 that is spaced from the pin 482 such that the lever 484 is rotated the cam 475 asserting a force along the longitudinal axis 473.

The lever 484 and the handle 406 may be adapted to prevent the lever 484 from rotating in the direction of arrow 486. Such rotation would cause the lever 484 and the shaft 414 to rotate about centerline 473 with respect to the handle 406. As the lever 484 is rotated in the direction of arrow 486, the cam 422 likewise rotates in the direction of arrow 486. The first jaw 418 and the second jaw 420 thus move in the direction of arrows 471 causing the jaws 418 and 420 to penetrate the liner 40.

As shown in FIG. 26, to operate the extraction device 400, the lever 484 is rotated about the centerline 473 of the extraction device 400 from first position 481 of the lever 484 as shown in solid to second position 483 of the lever 484 as shown in dash line 483. When the lever 484 is in the second position 483, the jaws 418 and 420 have engaged with the liner 484.

After the jaws 418 and 420 have engaged with the liner 40, the lever 484 is advanced in the direction of arrow 487 from second position 483 to third position 485 as shown in phantom. The handle 406 moves in a single motion for single purpose; to engage jaws 418 and 420 and liner 40. Once engaged, the T-handle 406 is rotated to remove liner 40.

The jaws 418 and 420 may have any suitable shape capable of penetrating the liner 40. For example and is shown in FIG. 26A, the jaws 418 and 420 may include a plurality of spaced apart ribs 441. As shown in FIG. 26A, the ribs 441 may extend substantially along periphery 443 of the jaws 418 and 420. The jaws 418 and 420 may include, for example, 2, 3, 4 or 5 spaced apart ribs 481.

Referring now to FIG. 26B, the extraction device of the present invention may be in the form of extraction device 400B having first and second jaws 418B and 420B. The jaws 418B and 420B may be similar to the jaws 418 and 420 of the extraction device 400 except that instead of having the ribs 441 of the extraction device 400, the extraction device 400B may include nibs or knurls 441B formed on periphery 443B of the jaws 418B and 420B.

Figure 27:
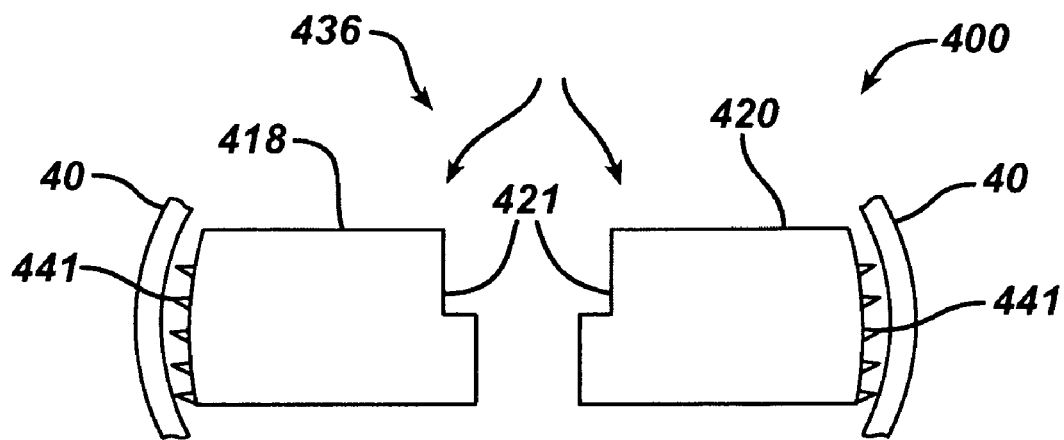
FIG. 27 is an enlarged plan view of the jaws of the acetabular liner extraction device of FIG. 26.
Figure 28:
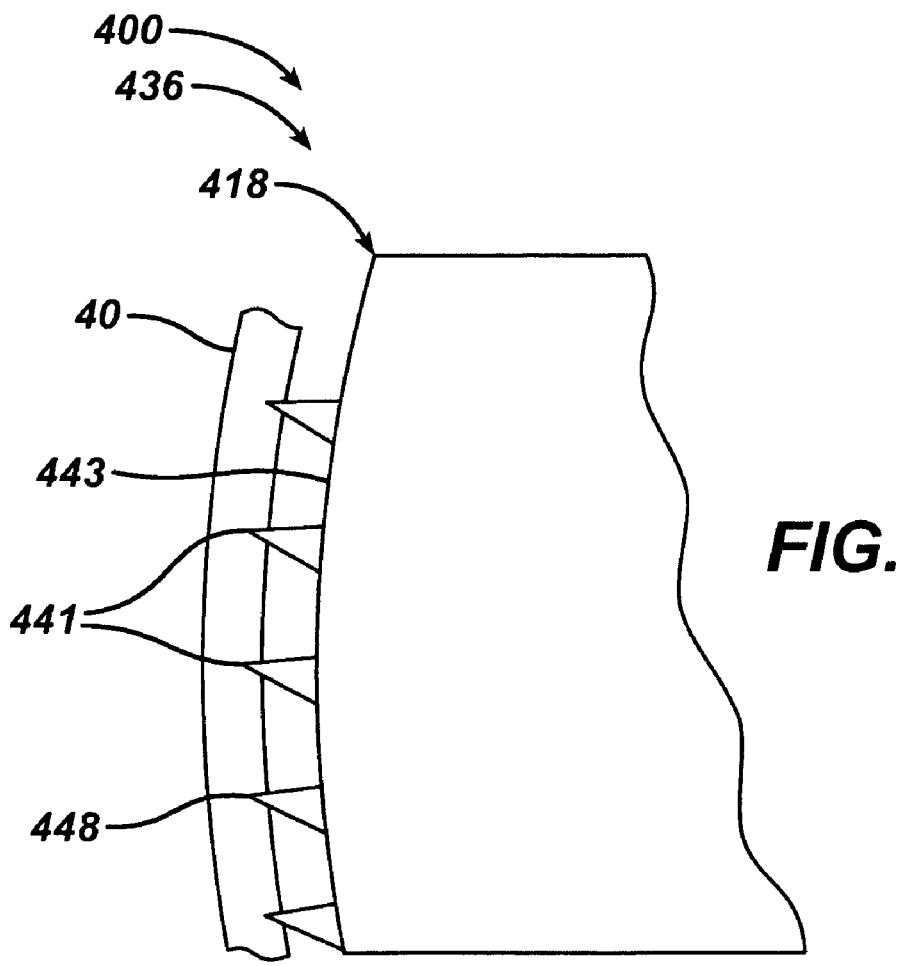
FIG. 28 is a partial enlarged plan view of the jaws of the acetabular liner extraction device of FIG. 26.
Figure 29:
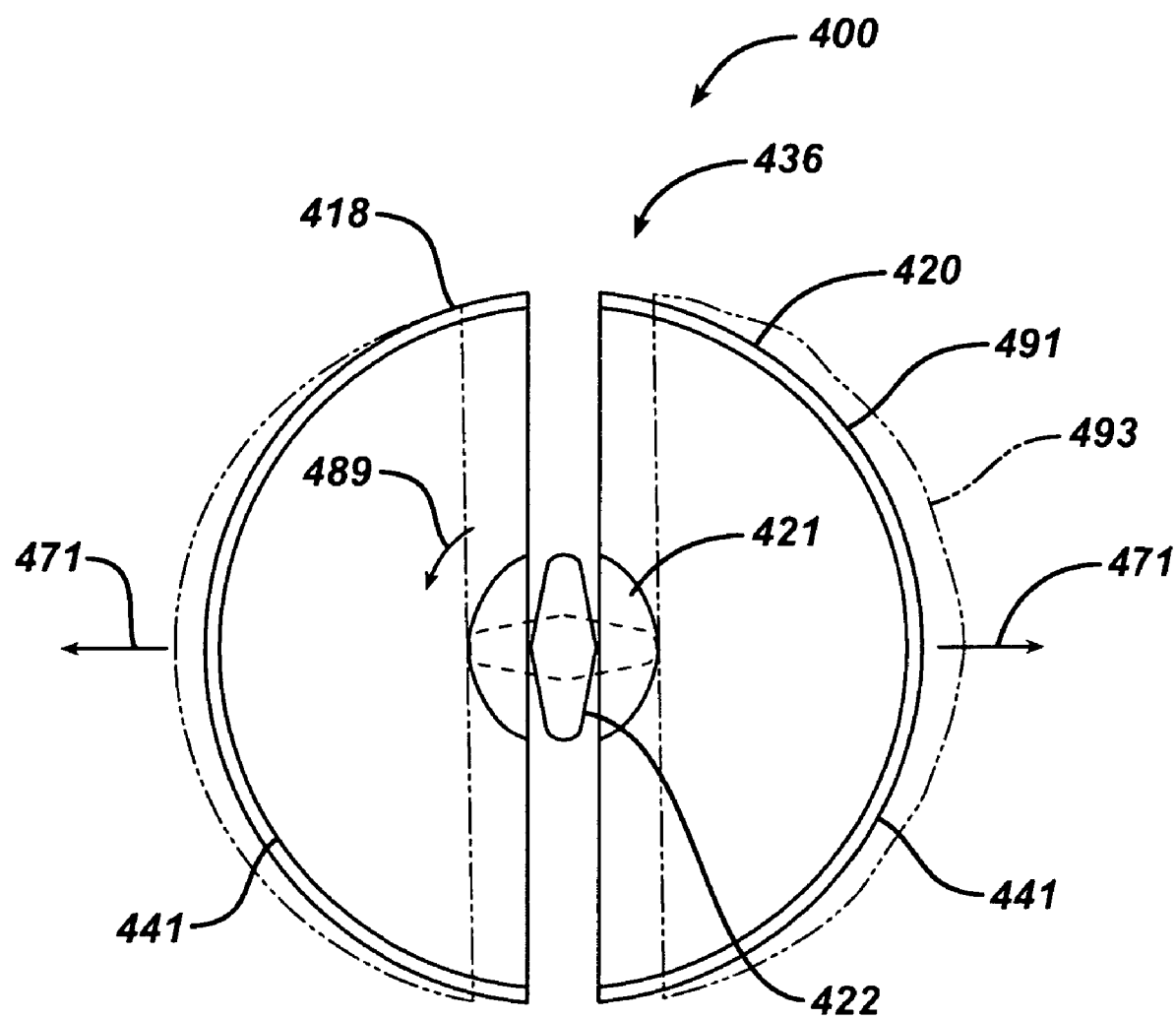
FIG. 29 is a bottom view of the jaws of the device of FIG. 26.

Referring now to FIGS. 27, 28, and 29 the jaws 418 and 420 of the jaw assembly 436 is shown in greater detail. Referring now to FIG. 28, the jaw assembly 436 of the extraction device 400 includes first jaw 418. The first jaw 418 includes a plurality of spaced apart ribs 441. The ribs 441 include a point 448 for penetration into liner 40 of the acetabular cup 32. The points 448 may be slightly flat, flattened, have a radius, or have an essentially sharp point. The ribs 441 may include a plurality of ribs such as two ribs, three ribs, four ribs, or five ribs or more. The ribs 441 may be equally spaced about periphery 443 of the jaw 418.

Referring now to FIG. 27, the first jaw 418 is shown in cooperation with second jaw 420 to form jaw assembly 436. The jaws 418 and 420 include inner periphery 421 for cooperation with the cam 422. The jaws 418 and 420 include the ribs 441 for penetration into the liner 40.

Referring now to FIG. 29, the jaw assembly 436 is shown with the jaws 418 and 420 in cooperation with the cam 422. The first jaw 418 and 420 are shown in first position 491 as shown in solid when the jaws 418 and 420 are in their most adjacent position. In this most adjacent position, the jaw assembly 236 and the extraction device 400 may be inserted into the acetabular cup 32.

The jaw assembly 436 is also shown with the jaws 418 and second jaw 420 in second position 493 as shown in phantom. In the second position 493, the cam 422 is rotated in the direction of arrow 489 approximately 90° such that the cam 422 engages inner periphery 421 of the jaws 418 and 420. The jaws then expand outwardly in the direction of arrows 471 such that ribs 441 of the jaws 418 and 420 penetrate liner 40.

Figure 30:
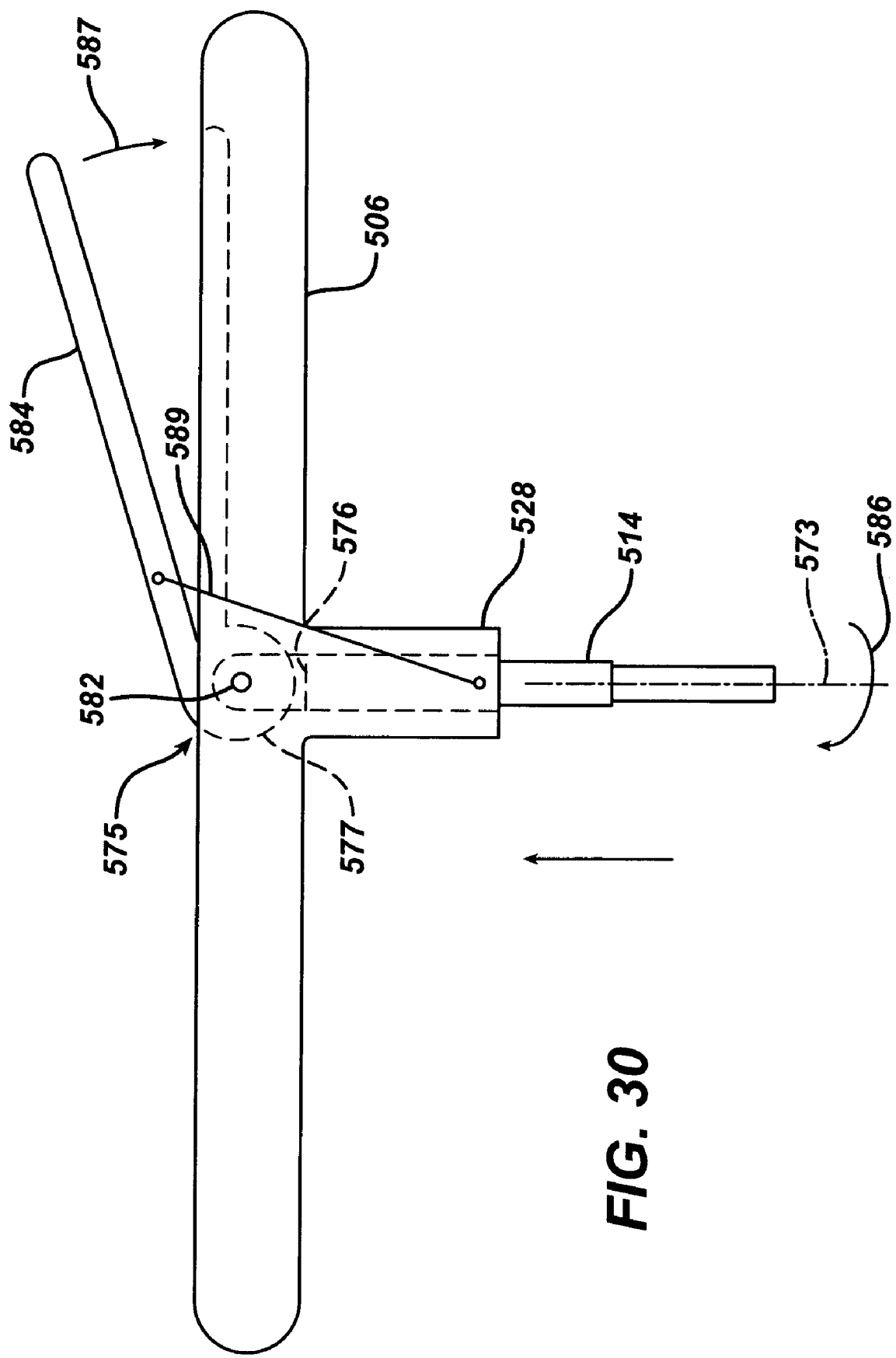
FIG. 30 is plan view, partially in cross section, of an acetabular liner extraction device according to another embodiment of the present invention.

Referring now to FIG. 30, yet another embodiment of the present invention is shown as extraction device 500.

The extraction device 500 of FIG. 30 is similar to the extraction device 400 of FIGS. 24-29. The extraction device 500 however includes a cam 575, which is somewhat different than the cam 475 of the extraction device 400. The cam 575 of the extraction device 500 has a periphery that is elliptical or oval rather than circular. The extraction device 500 includes a shaft 514 that is used to cause the jaws to expand into the liner and to cause the liner to be extracted from the shell. The shaft 514 permitted to rotated in the direction of arrow 586 and translate in the direction of arrow 588 within the body 528 of handle 506. Lever 584 is pivotally connected to the handle 506 about pin 582. The cam 575 defines a periphery 577 thereof, which is in sliding contact with end 576 of the shaft 514.

The shaft 514 may have a swivel joint that allows the shaft to rotate during extraction of liner. As the lever 584 rotates in the direction of arrow 586, the shaft 514 may likewise rotate in the direction of arrow 586 to actuate a cam similar to the cam 422 of the extractor device 400 of FIG. 26. As the link 589 connected to the lever 584 and the shaft 514 causes the shaft 514 to advance upwardly in the direction of arrow 588 to engage jaws with liner. The T-handle is then rotated to produce axial force to remove liner 40.

Figure 31:
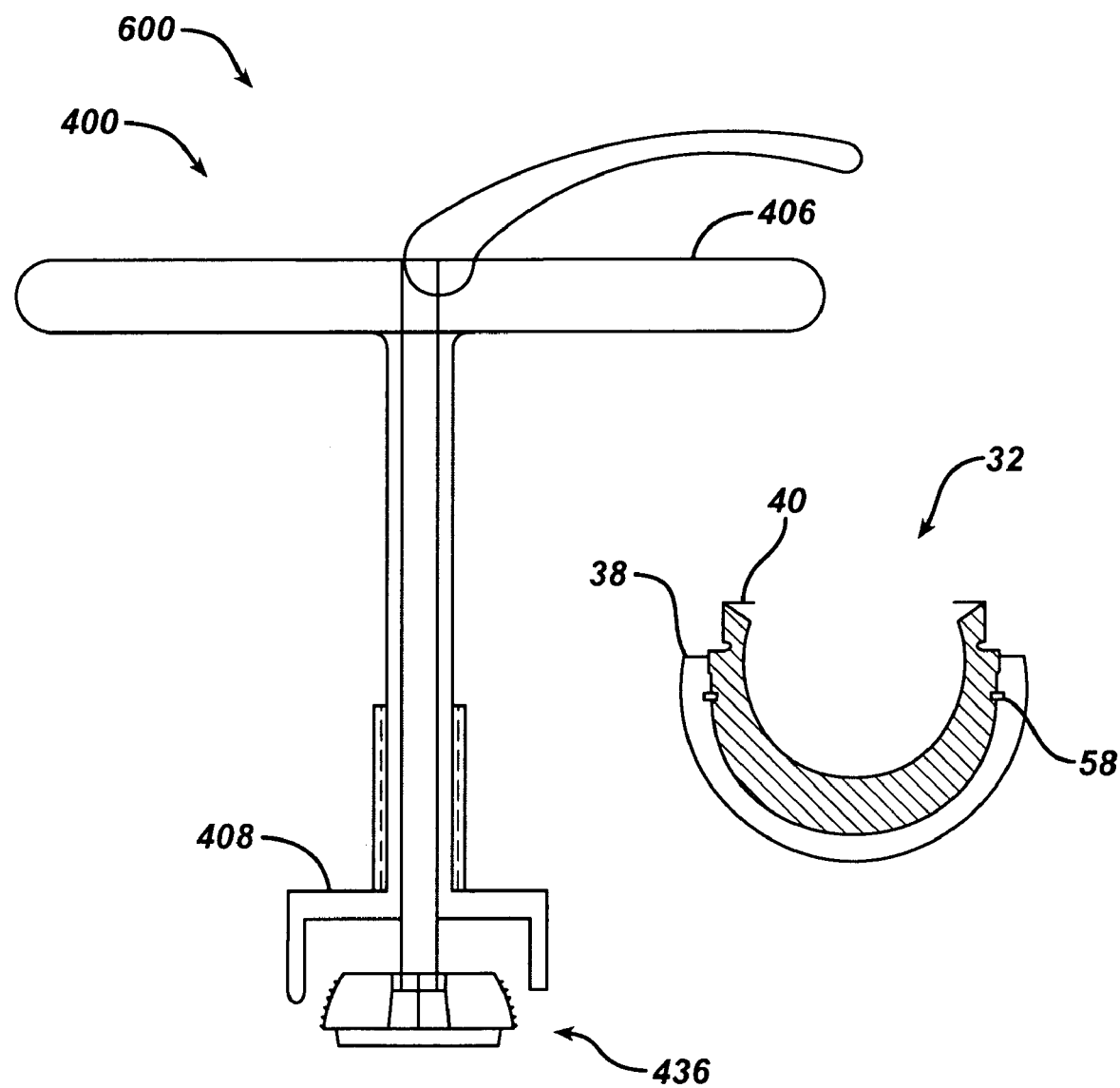
FIG. 31 is a plan view of a kit for performing hip arthroplasty according to the present invention.

Referring now to FIG. 31, yet another embodiment of the present invention is shown as kit 600. The kit 600 includes cup 32 including liner 40, shell 38, and snap ring 58 fitted between the liner 40 and the shell 38 for securing the liner 40 to the shell 38. The kit 600 further includes an extraction device 400. The extraction device 400 further includes base 408, handle 406 extending from the base 408, and jaws 436 operably connected to the base 408.

Referring now to FIG. 32, yet another embodiment of the present invention is shown as method 700 for performing orthopaedic revision surgery. The method 700 includes a first step 710 of inspecting an implanted acetabular cup assembly including a shell and a polymer liner in vivo in the patient. The method 700 further includes a second step 712 of determine if the polymer liner should be replaced from the shell of the acetabular cup assembly.

The method 700 further includes a third step 706 of providing an extraction device for removing the liner from the shell. The extraction device includes a jaw for cooperation with the liner. The jaw includes a portion of the jaw for penetrating into the liner. The extraction device also includes a handle operably associated with the jaw. The handle is adapted for gripping the extraction device. The method 700 further includes a fourth step 716 of extracting the liner from the shell with the extraction device while the shell is still implanted in the patient.

Referring now to FIG. 33, yet another embodiment of the present invention is shown as method 800 for performing orthopaedic revision surgery. The method 800 includes a first step 810 of inspecting an implanted acetabular cup assembly including a shell, a polymer lining, and a snap ring in vivo in a patient. The method 800 further includes a second step 812 of determining if the polymer liner should be replaced from the shell of the acetabular cup assembly.

The method 800 further includes a third step 814 of providing a distraction device for removing the liner from the shell. The extraction device includes a jaw for cooperation with the liner. The method 800 further includes a fourth step 816 of extracting the liner and the snap ring from the shell simultaneously with the extraction device while the shell is still implanted in the patient.

Although the present invention and its advantages have been described in detail, it should be understood that various changes, substitutions, and alterations can be made therein without departing from the spirit and scope of the present invention as defined by the appended claims.

We claim:

1. An extraction device for removing a liner from an acetabular cup, said extraction device comprising:
   a body;
   an actuator operably connected to said body, the actuator including a shaft and a spring;
   a jaw for cooperation with the liner, said jaw including a portion thereof for penetrating into the liner, said jaw operably connected to said actuator, said actuator adapted to cooperate with said jaw to provide a first position for said jaw spaced from the liner and a second position for said jaw in contact with the liner, wherein as the shaft is moved longitudinally away from the liner, the jaws are extended radially to be in contact with the liner; and
   a frame coupled to the actuator, at least a portion of the frame sized and shaped to abut the acetabular cup while the jaw is penetrating the liner;
   wherein the spring is coupled to the jaw and the frame and sized and shaped to urge the jaw in a direction away from the frame.

2. The extraction device of claim 1, wherein said jaw comprises a plurality of spaced apart jaw components.

3. The extraction device of claim 1, wherein the portion of said jaw for penetrating into the liner comprises a tapered protrusion.

4. The extraction device of claim 3, wherein the tapered protrusion comprise a tip having a length of less that 0.01 millimeters.

5. The extraction device of claim 3, wherein the tapered protrusion has a height of from about 1 millimeter to 5 millimeters.

6. The extraction device of claim 1, wherein said jaw and said actuator cooperate to provide a first position for said jaw spaced from the liner and a second position for said jaw in contact with the liner.

7. The extraction device of claim 1, further comprising a handle connected to said actuator for manually extracting the liner.

8. The extraction device of claim 1, wherein said jaw and said actuator comprise a cam connection there between to provide motion between said jaw and said handle.

9. The extraction device of claim 1, wherein said jaw and said actuator comprise a tapered connection there between to provide motion between said jaw and said handle.

10. The extraction device of claim 1, wherein said jaw and said actuator comprise a threaded connection there between to provide motion between said jaw and said handle.

11. The extraction device of claim 1:
further comprising a handle operably associated with said actuator, said handle defining an aperture therethrough, the aperture defining a longitudinal axis thereof; and
wherein said actuator comprises a portion thereof moveably positioned in the aperture.

12. The extraction device of claim 11, wherein said jaw and said actuator comprise a threaded connection there between to provide motion between said jaw and said handle.

13. The extraction device of claim 1, wherein said jaw is generally cylindrical.

14. The extraction device of claim 1, wherein said jaw has a shape that is generally a truncated sphere, truncated on both opposed poles of the sphere and defining an arcuate periphery therebetween.

15. The extraction device of claim 1:
wherein a portion of said jaw is adapted for penetrating into the liner; and
wherein said portion is positioned on the arcuate periphery of the jaw.

\* \* \* \* \*